United States Patent
Howell

(10) Patent No.: US 11,452,848 B2
(45) Date of Patent: Sep. 27, 2022

(54) CATHETER SECUREMENT DEVICE INCLUDING EXTENDED ANCHOR PAD AND RELEASE LINER CLASPING FEATURES

(71) Applicant: Bard Access Systems, Inc., Salt Lake City, UT (US)

(72) Inventor: Glade H. Howell, Draper, UT (US)

(73) Assignee: Bard Access Systems, Inc., Salt Lake City, UT (US)

(*) Notice: Subject to any disclaimer, the term of this patent is extended or adjusted under 35 U.S.C. 154(b) by 69 days.

(21) Appl. No.: 16/851,031

(22) Filed: Apr. 16, 2020

(65) Prior Publication Data

US 2020/0330733 A1     Oct. 22, 2020

Related U.S. Application Data

(60) Provisional application No. 62/835,312, filed on Apr. 17, 2019.

(51) Int. Cl.
*A61M 25/06*     (2006.01)
*A61M 25/02*     (2006.01)

(52) U.S. Cl.
CPC ........ *A61M 25/0637* (2013.01); *A61M 25/02* (2013.01); *A61M 2025/024* (2013.01); *A61M 2025/0253* (2013.01)

(58) Field of Classification Search
CPC .............. A61M 25/0637; A61M 25/02; A61M 2025/024; A61M 2025/0253;
(Continued)

(56) References Cited

U.S. PATENT DOCUMENTS 1,850,362 A * 3/1932 Vogel .................. G09F 1/10
                                                  40/124.4
3,589,361 A     6/1971 Loper et al.
(Continued)

FOREIGN PATENT DOCUMENTS

WO     9219309 A1     11/1992
WO     9421319 A1     9/1994
(Continued)

OTHER PUBLICATIONS

PCT/US2020/028583 filed Apr. 16, 2020 International Search Report and Written Opinion dated Jul. 27, 2020.
(Continued)

*Primary Examiner* — Quynh-Nhu H. Vu
(74) *Attorney, Agent, or Firm* — Rutan & Tucker LLP

(57) ABSTRACT

Embodiments disclosed herein are directed to a securement device including a retainer defining a channel and at least one mounting wing extending therefrom. The mounting wing extends distally of an insertion site a skin surface adjacent to the insertion site to prevent "rocking" or "pistoning." The mounting wing further includes channels of reduced thickness configured to impart malleable properties on the mounting wing. This can allow the mounting wing to be shaped to fit different portions of the patient. The retainer further includes various locking and anti-rotational features to guide the catheter into position within the retainer and further prevent "rocking" or "pistoning." The securement device also includes a protective pad to inhibit abrasions from a medical line, spin nuts, and the like, and includes a clasping feature to retain a portion of the release liner to prevent obstructing ingress/egress of the catheter.

31 Claims, 12 Drawing Sheets

(58) Field of Classification Search
CPC .. A61M 2025/0266; A61M 2025/0273; A61M 5/14248; A61F 13/0259; A61F 13/0263; A61F 13/0266; B42F 3/02; B42F 3/04; B42F 5/06; B42F 3/00; B42F 3/003; B42F 3/006

See application file for complete search history.

(56) References Cited

U.S. PATENT DOCUMENTS

| | | | |
|---|---|---|---|
| 3,605,725 A | 9/1971 | Bentov | |
| 3,900,026 A | 8/1975 | Wagner | |
| 3,901,226 A | 8/1975 | Scardenzan | |
| 3,921,631 A | 11/1975 | Thompson | |
| 3,973,565 A | 8/1976 | Steer | |
| 4,161,177 A | 7/1979 | Fuchs | |
| 4,224,937 A | 9/1980 | Gordon | |
| 4,250,880 A | 2/1981 | Gordon | |
| 4,362,156 A | 12/1982 | Feller, Jr. et al. | |
| 4,397,641 A | 8/1983 | Jacobs | |
| 4,435,174 A | 3/1984 | Redmond et al. | |
| 4,457,754 A | 7/1984 | Buttaravoli | |
| 4,490,141 A | 12/1984 | Lacko et al. | |
| 4,534,762 A | 8/1985 | Heyer | |
| 4,579,120 A | 4/1986 | MacGregor | |
| 4,614,183 A * | 9/1986 | McCracken | A61F 13/023 602/57 |
| 4,645,492 A | 2/1987 | Weeks | |
| 4,711,636 A | 12/1987 | Bierman | |
| 4,743,232 A | 5/1988 | Kruger | |
| 4,834,712 A | 5/1989 | Quinn et al. | |
| 4,838,868 A | 6/1989 | Forgar et al. | |
| 4,915,694 A | 4/1990 | Yamamoto et al. | |
| 4,976,700 A * | 12/1990 | Tollini | A61M 25/02 128/877 |
| 5,192,273 A | 3/1993 | Bierman | |
| 5,192,274 A | 3/1993 | Bierman | |
| 5,267,968 A | 12/1993 | Russo | |
| 5,290,248 A | 3/1994 | Bierman et al. | |
| 5,314,411 A | 5/1994 | Bierman et al. | |
| 5,318,546 A | 6/1994 | Bierman | |
| 5,330,461 A | 7/1994 | Leeker | |
| 5,354,282 A | 10/1994 | Bierman | |
| 5,395,344 A | 3/1995 | Beisang, III et al. | |
| 5,413,562 A | 5/1995 | Swauger | |
| 5,456,671 A | 10/1995 | Bierman | |
| 5,484,420 A | 1/1996 | Russo | |
| 5,554,106 A | 9/1996 | Layman-Spillar et al. | |
| D375,355 S * | 11/1996 | Bierman | D24/128 |
| D375,356 S * | 11/1996 | Bierman | A61M 25/02 D24/128 |
| 5,578,013 A | 11/1996 | Bierman | |
| 5,626,565 A | 5/1997 | Landis et al. | |
| 5,637,098 A | 6/1997 | Bierman | |
| 5,686,096 A | 11/1997 | Khan et al. | |
| 5,693,032 A | 12/1997 | Bierman | |
| 5,702,371 A | 12/1997 | Bierman | |
| 5,722,959 A | 3/1998 | Bierman | |
| 5,800,402 A | 9/1998 | Bierman | |
| 5,810,781 A * | 9/1998 | Bierman | A61M 25/02 604/174 |
| 5,827,230 A | 10/1998 | Bierman | |
| 5,833,663 A | 11/1998 | Bierman et al. | |
| 5,833,665 A | 11/1998 | Bootman et al. | |
| 5,833,667 A | 11/1998 | Bierman | |
| D404,815 S | 1/1999 | Bierman | |
| 5,855,591 A | 1/1999 | Bierman | |
| 5,941,263 A | 8/1999 | Bierman | |
| 5,947,931 A | 9/1999 | Bierman | |
| D425,619 S * | 5/2000 | Bierman | A61M 25/02 D24/128 |
| 6,117,163 A | 9/2000 | Bierman | |
| 6,132,398 A | 10/2000 | Bierman | |
| 6,213,979 B1 * | 4/2001 | Bierman | A61M 25/02 128/DIG. 26 |
| 6,224,571 B1 | 5/2001 | Bierman | |
| 6,273,873 B1 | 8/2001 | Fleischer | |
| 6,283,945 B1 * | 9/2001 | Bierman | A61M 25/02 604/174 |
| 6,290,676 B1 | 9/2001 | Bierman | |
| 6,302,867 B1 | 10/2001 | Brown, Jr. et al. | |
| 6,361,523 B1 | 3/2002 | Bierman | |
| 6,413,240 B1 | 7/2002 | Bierman et al. | |
| 6,428,515 B1 | 8/2002 | Bierman et al. | |
| 6,428,516 B1 | 8/2002 | Bierman | |
| 6,436,073 B1 | 8/2002 | Von Teichert | |
| 6,447,485 B2 | 9/2002 | Bierman | |
| 6,482,183 B1 | 11/2002 | Pausch et al. | |
| 6,491,664 B2 | 12/2002 | Bierman | |
| D470,936 S | 2/2003 | Bierman | |
| 6,551,284 B1 | 4/2003 | Greenberg et al. | |
| 6,551,285 B1 | 4/2003 | Bierman | |
| 6,572,588 B1 | 6/2003 | Bierman et al. | |
| 6,582,403 B1 | 6/2003 | Bierman et al. | |
| 6,663,600 B2 | 12/2003 | Bierman et al. | |
| 6,673,046 B2 | 1/2004 | Bierman et al. | |
| 6,689,104 B2 | 2/2004 | Bierman | |
| D492,411 S | 6/2004 | Bierman | |
| 6,770,055 B2 | 8/2004 | Bierman et al. | |
| 6,786,892 B2 | 9/2004 | Bierman | |
| 6,796,310 B2 | 9/2004 | Bierman | |
| 6,827,705 B2 | 12/2004 | Bierman | |
| 6,827,706 B2 | 12/2004 | Tollini | |
| 6,827,707 B2 | 12/2004 | Wright et al. | |
| 6,837,875 B1 | 1/2005 | Bierman | |
| 6,866,652 B2 | 3/2005 | Bierman | |
| D503,977 S | 4/2005 | Bierman | |
| 6,929,625 B2 | 8/2005 | Bierman | |
| 6,948,500 B2 | 9/2005 | Bierman | |
| 6,951,550 B2 | 10/2005 | Bierman | |
| 6,972,003 B2 | 12/2005 | Bierman et al. | |
| 6,979,320 B2 | 12/2005 | Bierman | |
| 7,014,627 B2 | 3/2006 | Bierman | |
| 7,018,362 B2 | 3/2006 | Bierman et al. | |
| 7,025,749 B2 * | 4/2006 | Propp | A61M 25/02 604/180 |
| 7,094,944 B2 | 8/2006 | Faasse, Jr. | |
| D528,206 S | 9/2006 | Bierman | |
| 7,147,620 B2 | 12/2006 | Kessler et al. | |
| 7,153,291 B2 | 12/2006 | Bierman | |
| 7,204,827 B2 | 4/2007 | Kessler | |
| 7,223,256 B2 | 5/2007 | Bierman | |
| D547,862 S | 7/2007 | Dikeman et al. | |
| 7,247,150 B2 | 7/2007 | Bierman | |
| D552,732 S | 10/2007 | Bierman et al. | |
| 7,316,679 B2 | 1/2008 | Bierman | |
| 7,317,134 B2 | 1/2008 | Faasse, Jr. | |
| D563,552 S | 3/2008 | Bierman et al. | |
| D567,941 S | 4/2008 | Dikeman et al. | |
| 7,354,421 B2 | 4/2008 | Bierman | |
| D568,466 S | 5/2008 | Dikeman et al. | |
| D569,506 S | 5/2008 | Dikeman et al. | |
| D577,437 S | 9/2008 | Bierman et al. | |
| 7,491,190 B2 | 2/2009 | Bierman et al. | |
| 7,520,870 B2 | 4/2009 | Bierman | |
| 7,563,251 B2 | 7/2009 | Bierman et al. | |
| 7,568,484 B2 | 8/2009 | Bierman et al. | |
| 7,578,804 B2 | 8/2009 | Bierman | |
| 7,591,803 B2 | 9/2009 | Bierman | |
| 7,611,493 B2 | 11/2009 | Jonsson | |
| 7,626,070 B2 | 12/2009 | Propp | |
| 7,628,154 B2 | 12/2009 | Bierman et al. | |
| 7,628,771 B2 | 12/2009 | Kessler | |
| 7,635,355 B2 | 12/2009 | Bierman | |
| 7,648,492 B2 | 1/2010 | Bierman | |
| 7,651,479 B2 | 1/2010 | Bierman | |
| 7,660,615 B2 | 2/2010 | VanAntwerp et al. | |
| 7,666,167 B2 | 2/2010 | Bierman | |
| D613,857 S | 4/2010 | Bierman | |
| D613,858 S | 4/2010 | Bierman | |
| D613,859 S | 4/2010 | Bierman | |
| D613,860 S | 4/2010 | Bierman et al. | |
| 7,690,608 B2 | 4/2010 | Huber | |
| 7,691,096 B2 | 4/2010 | Gillis | |

(56) References Cited

U.S. PATENT DOCUMENTS

| | | | |
|---|---|---|---|
| 7,722,571 B2 | 5/2010 | Bierman et al. |
| 7,723,561 B2 | 5/2010 | Propp |
| D618,792 S | 6/2010 | Bierman |
| 7,744,572 B2 | 6/2010 | Bierman |
| 7,758,586 B2 | 7/2010 | Muto et al. |
| 7,762,991 B2 | 7/2010 | Bierman et al. |
| D622,841 S | 8/2010 | Bierman |
| 7,780,634 B2 | 8/2010 | Propp |
| 7,785,295 B2 | 8/2010 | Bierman |
| 7,799,001 B2 | 9/2010 | Bierman |
| 7,806,873 B2 | 10/2010 | Dikeman et al. |
| 7,811,258 B2 | 10/2010 | Bierman |
| 7,837,655 B2 | 11/2010 | Bierman et al. |
| D629,512 S | 12/2010 | Bierman et al. |
| D629,513 S | 12/2010 | Bierman et al. |
| D629,514 S | 12/2010 | Bierman |
| 7,879,013 B2 | 2/2011 | Smith et al. |
| 7,887,515 B2 | 2/2011 | Bierman |
| 7,935,083 B2 | 5/2011 | Bierman et al. |
| 7,935,084 B2 | 5/2011 | Bierman |
| 7,955,307 B2 | 6/2011 | Bierman et al. |
| 7,967,792 B2 | 6/2011 | Bierman |
| 7,972,310 B2 | 7/2011 | Kessler |
| 7,981,087 B2 | 7/2011 | Gesler, III |
| 7,985,205 B2 | 7/2011 | Adams |
| 7,985,206 B2 | 7/2011 | Dikeman et al. |
| 7,988,673 B2 | 8/2011 | Wright et al. |
| 8,016,792 B2 | 9/2011 | Wright et al. |
| 8,016,793 B2 | 9/2011 | Wright et al. |
| 8,025,060 B2 | 9/2011 | Bierman |
| 8,025,643 B2 | 9/2011 | Bierman |
| 8,043,280 B2 | 10/2011 | Bierman |
| 8,052,648 B2 | 11/2011 | Dikeman et al. |
| 8,052,649 B2 | 11/2011 | Wright |
| 8,052,652 B2 | 11/2011 | Bierman et al. |
| 8,053,623 B2 | 11/2011 | Propp |
| 8,057,440 B2 | 11/2011 | Bierman |
| 8,074,651 B2 | 12/2011 | Bierman et al. |
| 8,100,862 B2 | 1/2012 | Bierman |
| 8,105,289 B2 | 1/2012 | Bierman et al. |
| 8,105,290 B2 | 1/2012 | Wright et al. |
| 8,114,054 B2 | 2/2012 | Bierman et al. |
| 8,128,602 B2 | 3/2012 | Tollini et al. |
| 8,146,210 B2 | 4/2012 | Nishtala |
| 8,157,770 B2 | 4/2012 | Elwell et al. |
| 8,162,898 B1 | 4/2012 | Wright |
| 8,172,807 B2 | 5/2012 | Dikeman et al. |
| 8,177,756 B2 | 5/2012 | Wright |
| 8,197,447 B2 | 6/2012 | Wright |
| 8,211,063 B2 | 7/2012 | Bierman et al. |
| 8,211,064 B2 | 7/2012 | Sloan |
| 8,212,101 B2* | 7/2012 | Propp ................. A61F 13/0269 602/41 |
| 8,241,253 B2 | 8/2012 | Bracken |
| 8,246,583 B2 | 8/2012 | Bierman |
| 8,251,956 B2 | 8/2012 | Bierman et al. |
| 8,269,059 B2 | 9/2012 | Wright et al. |
| 8,277,420 B2 | 10/2012 | Bierman et al. |
| 8,282,606 B2 | 10/2012 | Bierman |
| 8,298,191 B2 | 10/2012 | Bierman et al. |
| 8,333,736 B2 | 12/2012 | Wright et al. |
| 8,353,876 B2 | 1/2013 | Suwito et al. |
| 8,357,124 B2 | 1/2013 | Bierman |
| 8,366,678 B2 | 2/2013 | Bierman et al. |
| 8,394,065 B2 | 3/2013 | Bierman |
| 8,394,067 B2 | 3/2013 | Bracken et al. |
| 8,398,599 B2 | 3/2013 | Bierman |
| 8,425,467 B1 | 4/2013 | Haak |
| 8,465,458 B2 | 6/2013 | Bierman |
| 8,496,625 B2 | 7/2013 | Brugger et al. |
| 8,500,698 B2 | 8/2013 | Kyvik et al. |
| 8,506,531 B2 | 8/2013 | Bierman |
| 8,540,680 B2 | 9/2013 | Burn |
| 8,579,863 B2 | 11/2013 | Scherr |
| 8,585,655 B2 | 11/2013 | Bierman |
| 8,608,704 B2 | 12/2013 | Bierman |
| 8,608,705 B2 | 12/2013 | Peters et al. |
| 8,608,706 B2 | 12/2013 | Davis et al. |
| 8,636,698 B2 | 1/2014 | Bierman et al. |
| 8,636,701 B2 | 1/2014 | Henry et al. |
| 8,641,678 B2 | 2/2014 | Bierman |
| 8,657,791 B2 | 2/2014 | Bierman et al. |
| 8,663,266 B1 | 3/2014 | Obsuth |
| 8,679,066 B2 | 3/2014 | Aviles |
| 8,679,067 B2 | 3/2014 | Wright |
| 8,684,976 B2 | 4/2014 | Bierman et al. |
| 8,708,967 B2 | 4/2014 | Bierman |
| 8,728,039 B2 | 5/2014 | Bierman et al. |
| 8,734,400 B2 | 5/2014 | Ciccone |
| 8,740,852 B2 | 6/2014 | Aviles |
| 8,747,360 B2 | 6/2014 | Peterson et al. |
| 8,795,237 B2 | 8/2014 | Vitaris et al. |
| 8,821,448 B2 | 9/2014 | Hawkins |
| 8,827,959 B2 | 9/2014 | Wright et al. |
| 8,827,960 B2 | 9/2014 | Haak |
| 8,834,424 B2 | 9/2014 | Parvatiyar et al. |
| 8,834,425 B2 | 9/2014 | Bracken et al. |
| 8,840,589 B2 | 9/2014 | Bierman et al. |
| 8,900,196 B2 | 12/2014 | Andino |
| 8,915,885 B2 | 12/2014 | Smith et al. |
| 8,945,062 B2 | 2/2015 | Waller |
| 8,969,649 B2 | 3/2015 | Leibowitz et al. |
| 8,986,257 B2 | 3/2015 | Rosenberg et al. |
| 9,017,290 B2 | 4/2015 | Peters et al. |
| 9,056,186 B2 | 6/2015 | Wright et al. |
| 9,061,122 B2 | 6/2015 | Bierman et al. |
| 9,067,013 B2 | 6/2015 | Wright et al. |
| 9,138,560 B2 | 9/2015 | Wright et al. |
| 9,155,866 B2 | 10/2015 | Bornhoft |
| 9,155,867 B2 | 10/2015 | Peterson et al. |
| 9,220,870 B2 | 12/2015 | Hyman et al. |
| 9,238,123 B2 | 1/2016 | Weadock et al. |
| 9,248,259 B2 | 2/2016 | Kyvik et al. |
| 9,248,260 B2 | 2/2016 | Khalaj |
| 9,314,596 B2 | 4/2016 | Rosenberg et al. |
| 9,327,098 B2 | 5/2016 | Kelvered et al. |
| 9,358,366 B2 | 6/2016 | Kyvik et al. |
| 9,415,191 B2 | 8/2016 | Aviles |
| 9,421,344 B2 | 8/2016 | Hyman et al. |
| 9,457,169 B2 | 10/2016 | Peterson et al. |
| 9,468,740 B2 | 10/2016 | Bierman et al. |
| 9,480,821 B2 | 11/2016 | Ciccone et al. |
| 9,492,640 B2 | 11/2016 | Rosenhan |
| 9,526,871 B2 | 12/2016 | Wright et al. |
| 9,550,043 B2 | 1/2017 | Rosenberg et al. |
| 9,561,348 B2 | 2/2017 | Bierman |
| 9,604,034 B2 | 3/2017 | Andino |
| 9,616,200 B2 | 4/2017 | Smith et al. |
| 9,642,987 B2 | 5/2017 | Bierman et al. |
| 9,694,130 B2 | 7/2017 | Andino et al. |
| 9,700,700 B2 | 7/2017 | Andino et al. |
| 9,731,097 B2 | 8/2017 | Andino et al. |
| 9,962,524 B2 | 5/2018 | Andino |
| 9,974,929 B2 | 5/2018 | Ciccone et al. |
| 9,993,619 B2 | 6/2018 | Bracken et al. |
| 10,245,415 B2 | 4/2019 | Andino et al. |
| 10,322,262 B2 | 6/2019 | Bracken et al. |
| 10,426,928 B2 | 10/2019 | Andino et al. |
| 10,537,714 B2 | 1/2020 | Andino et al. |
| 10,561,815 B2 | 2/2020 | Bierman et al. |
| 10,589,067 B2 | 3/2020 | Ciccone |
| 2001/0007061 A1 | 7/2001 | Bierman |
| 2001/0000111 A1 | 8/2001 | Bierman |
| 2001/0039399 A1 | 11/2001 | Bierman |
| 2002/0026152 A1 | 2/2002 | Bierman |
| 2002/0068904 A1 | 6/2002 | Bierman et al. |
| 2002/0099360 A1 | 7/2002 | Bierman |
| 2002/0001331 A1 | 9/2002 | Bierman |
| 2002/0014329 A1 | 10/2002 | Taylor et al. |
| 2002/0165493 A1 | 11/2002 | Bierman |
| 2002/0165494 A1 | 11/2002 | Bierman et al. |
| 2002/0001882 A1 | 12/2002 | Bierman et al. |
| 2002/0187259 A1 | 12/2002 | Bierman |
| 2002/0188255 A1 | 12/2002 | Bierman et al. |

(56) References Cited

U.S. PATENT DOCUMENTS

| | | |
|---|---|---|
| 2002/0188257 A1 | 12/2002 | Bierman |
| 2003/0083625 A1 | 5/2003 | Bierman |
| 2003/0089374 A1 | 5/2003 | Bierman |
| 2003/0125668 A1 | 7/2003 | Bierman |
| 2003/0229313 A1 | 12/2003 | Bierman |
| 2004/0034330 A1 | 2/2004 | Bierman et al. |
| 2004/0102736 A1 | 5/2004 | Bierman |
| 2004/0138624 A1 | 7/2004 | Bierman |
| 2004/0001674 A1 | 8/2004 | Wright et al. |
| 2004/0199122 A1 | 10/2004 | Bierman et al. |
| 2004/0204684 A1 | 10/2004 | Bierman |
| 2004/0204685 A1 | 10/2004 | Wright et al. |
| 2004/0002265 A1 | 11/2004 | Bierman |
| 2005/0010173 A1 | 1/2005 | Bierman et al. |
| 2005/0027258 A1 | 2/2005 | Bierman et al. |
| 2005/0075610 A1 | 4/2005 | Bierman |
| 2005/0001313 A1 | 6/2005 | Bierman |
| 2005/0021595 A1 | 9/2005 | Rossen |
| 2005/0192539 A1 | 9/2005 | Bierman et al. |
| 2005/0192540 A1 | 9/2005 | Kessler |
| 2005/0263158 A1 | 12/2005 | Bierman |
| 2005/0273058 A1 | 12/2005 | Bierman |
| 2006/0004123 A1 | 2/2006 | Bowen |
| 2006/0041233 A1* | 2/2006 | Bowen .................. A61M 25/02 |
| | | 604/180 |
| 2006/0064063 A1 | 3/2006 | Bierman |
| 2006/0084922 A1 | 4/2006 | Botha |
| 2006/0089600 A1 | 4/2006 | Bierman et al. |
| 2006/0001241 A1 | 6/2006 | Bierman et al. |
| 2006/0001291 A1 | 6/2006 | Bierman et al. |
| 2006/0129103 A1 | 6/2006 | Bierman et al. |
| 2006/0135944 A1 | 6/2006 | Bierman |
| 2006/0184127 A1 | 8/2006 | Bierman |
| 2006/0184128 A1 | 8/2006 | Bierman |
| 2006/0184129 A1 | 8/2006 | Bierman |
| 2006/0247577 A1 | 11/2006 | Wright |
| 2006/0264836 A1* | 11/2006 | Bierman .............. A61M 25/02 |
| | | 604/180 |
| 2006/0270994 A1 | 11/2006 | Bierman |
| 2006/0270995 A1 | 11/2006 | Bierman |
| 2006/0276752 A1 | 12/2006 | Bierman et al. |
| 2007/0055205 A1 | 3/2007 | Wright et al. |
| 2007/0066958 A1 | 3/2007 | Wright |
| 2007/0068533 A1 | 3/2007 | Bierman et al. |
| 2007/0088329 A1 | 4/2007 | Bierman |
| 2007/0125483 A1* | 6/2007 | Barnett .................. A61K 9/703 |
| | | 156/152 |
| 2007/0142784 A1 | 6/2007 | Dikeman et al. |
| 2007/0149930 A1 | 6/2007 | Bierman |
| 2007/0156097 A1 | 7/2007 | Bierman |
| 2007/0167915 A1 | 7/2007 | Bierman |
| 2007/0173766 A1 | 7/2007 | Bierman |
| 2007/0173769 A1 | 7/2007 | Kessler |
| 2007/0219500 A1 | 9/2007 | Wright et al. |
| 2007/0002763 A1 | 11/2007 | Bierman |
| 2007/0265571 A1 | 11/2007 | Utterberg et al. |
| 2007/0265572 A1 | 11/2007 | Smith et al. |
| 2007/0276332 A1 | 11/2007 | Bierman |
| 2007/0276334 A1 | 11/2007 | Bierman et al. |
| 2007/0276335 A1 | 11/2007 | Bierman |
| 2007/0276336 A1 | 11/2007 | Bierman et al. |
| 2007/0282273 A1 | 12/2007 | Bierman |
| 2007/0287963 A1 | 12/2007 | Bierman |
| 2008/0027391 A1 | 1/2008 | Bierman |
| 2008/0027392 A1 | 1/2008 | Bierman |
| 2008/0027393 A1 | 1/2008 | Bierman |
| 2008/0027394 A1 | 1/2008 | Bierman |
| 2008/0039798 A1 | 2/2008 | Bierman |
| 2008/0077118 A1 | 3/2008 | Bierman |
| 2008/0097334 A1 | 4/2008 | Dikeman et al. |
| 2008/0132848 A1 | 6/2008 | Wright et al. |
| 2008/0154208 A1 | 6/2008 | Bierman |
| 2008/0020088 A1 | 8/2008 | Kyvik et al. |
| 2008/0249476 A1 | 10/2008 | Bierman et al. |
| 2008/0029411 A1 | 11/2008 | Schwartz et al. |
| 2009/0000368 A1 | 2/2009 | Bierman |
| 2009/0000432 A1 | 2/2009 | Bierman |
| 2009/0000937 A1 | 4/2009 | Bierman et al. |
| 2009/0093769 A1 | 4/2009 | Wright et al. |
| 2009/0137961 A1 | 5/2009 | Bracken |
| 2009/0137962 A1 | 5/2009 | Bracken et al. |
| 2009/0139061 A1 | 6/2009 | Nishtala |
| 2009/0143740 A1 | 6/2009 | Bierman et al. |
| 2009/0143741 A1 | 6/2009 | Burn |
| 2009/0143742 A1 | 6/2009 | Bracken et al. |
| 2009/0143744 A1 | 6/2009 | Bierman et al. |
| 2009/0145440 A1 | 6/2009 | Bierman et al. |
| 2009/0182283 A1* | 7/2009 | Sloan .................... A61M 25/02 |
| | | 604/180 |
| 2009/0019819 A1 | 8/2009 | Jensen et al. |
| 2009/0254040 A1 | 10/2009 | Bierman et al. |
| 2009/0259188 A1 | 10/2009 | Bierman et al. |
| 2009/0003264 A1 | 12/2009 | Bierman et al. |
| 2009/0032647 A1 | 12/2009 | Bierman et al. |
| 2009/0306603 A1 | 12/2009 | Bierman et al. |
| 2010/0022962 A1 | 1/2010 | Bierman et al. |
| 2010/0100051 A1 | 4/2010 | Bierman |
| 2010/0114034 A1 | 5/2010 | Wright et al. |
| 2010/0137807 A1 | 6/2010 | Kessler |
| 2010/0001794 A1 | 7/2010 | Bierman et al. |
| 2010/0001809 A1 | 7/2010 | Talsma et al. |
| 2010/0179482 A1 | 7/2010 | Wright et al. |
| 2010/0179483 A1 | 7/2010 | Wright et al. |
| 2010/0222748 A1 | 9/2010 | Bierman et al. |
| 2010/0002987 A1 | 11/2010 | Nishtala |
| 2010/0298778 A1 | 11/2010 | Bracken et al. |
| 2010/0324491 A1 | 12/2010 | Bierman et al. |
| 2011/0021998 A1 | 1/2011 | Dikeman et al. |
| 2011/0000544 A1 | 3/2011 | Nishtala |
| 2011/0112483 A1 | 5/2011 | Smith et al. |
| 2011/0152778 A1* | 6/2011 | Gyrn .................... A61F 13/023 |
| | | 604/180 |
| 2011/0001784 A1 | 7/2011 | Bierman et al. |
| 2011/0016652 A1 | 7/2011 | LeLievre et al. |
| 2011/0202010 A1 | 8/2011 | Bierman |
| 2011/0002133 A1 | 9/2011 | Bierman |
| 2011/0002184 A1 | 9/2011 | Bierman et al. |
| 2011/0021849 A1 | 9/2011 | Bierman et al. |
| 2011/0230843 A1 | 9/2011 | Bierman et al. |
| 2011/0002400 A1 | 10/2011 | Ciccone |
| 2011/0002457 A1 | 10/2011 | Andino et al. |
| 2011/0002576 A1 | 10/2011 | Kessler |
| 2011/0264050 A1 | 10/2011 | Henry et al. |
| 2011/0282291 A1 | 11/2011 | Ciccone |
| 2011/0282294 A1 | 11/2011 | Dikeman et al. |
| 2011/0288487 A1 | 11/2011 | Wright et al. |
| 2011/0288489 A1 | 11/2011 | Bierman et al. |
| 2011/0295173 A1 | 12/2011 | Wright et al. |
| 2011/0295210 A1 | 12/2011 | Wright |
| 2011/0313362 A1 | 12/2011 | Bierman |
| 2011/0319830 A1 | 12/2011 | Peters et al. |
| 2012/0000413 A1 | 2/2012 | Bierman |
| 2012/0000466 A1 | 2/2012 | Bierman |
| 2012/0041377 A1 | 2/2012 | Haak |
| 2012/0000535 A1 | 3/2012 | Bierman et al. |
| 2012/0000593 A1 | 3/2012 | Dikeman et al. |
| 2012/0059329 A1 | 3/2012 | Bierman |
| 2012/0071833 A1 | 3/2012 | Hill et al. |
| 2012/0010907 A1 | 5/2012 | Elsamahy et al. |
| 2012/0123343 A1 | 5/2012 | Aviles |
| 2012/0136299 A1 | 5/2012 | Constantineau et al. |
| 2012/0136314 A1 | 5/2012 | Ciccone et al. |
| 2012/0001501 A1 | 6/2012 | Andino |
| 2012/0143140 A1 | 6/2012 | Bierman et al. |
| 2012/0184915 A1 | 7/2012 | Bierman et al. |
| 2012/0002151 A1 | 8/2012 | Wright |
| 2012/0002209 A1 | 8/2012 | Dikeman et al. |
| 2012/0197202 A1 | 8/2012 | Wright et al. |
| 2012/0197205 A1 | 8/2012 | Peters |
| 2012/0226237 A1* | 9/2012 | Russo .................... A61M 25/02 |
| | | 604/177 |
| 2012/0232488 A1 | 9/2012 | Aviles |
| 2012/0232490 A1 | 9/2012 | Andino |
| 2012/0265147 A1 | 10/2012 | Andino et al. |

(56) References Cited

U.S. PATENT DOCUMENTS

| | | |
|---|---|---|
| 2012/0271237 A1 | 10/2012 | Andino |
| 2012/0271239 A1 | 10/2012 | Andino et al. |
| 2012/0271240 A1 | 10/2012 | Andino et al. |
| 2012/0316505 A1 | 12/2012 | Wright |
| 2013/0000183 A1 | 1/2013 | Wright et al. |
| 2013/0053785 A1 | 2/2013 | Parvatiyar et al. |
| 2013/0079723 A1 | 3/2013 | Andino et al. |
| 2013/0009650 A1 | 4/2013 | LeLievre |
| 2013/0001380 A1 | 5/2013 | Bierman |
| 2013/0138080 A1 | 5/2013 | Andino et al. |
| 2013/0015079 A1 | 6/2013 | Souza et al. |
| 2013/0150827 A1 | 6/2013 | Bracken et al. |
| 2013/0345639 A1 | 12/2013 | Spittier |
| 2014/0142538 A1 | 5/2014 | Hyman et al. |
| 2014/0188078 A1 | 7/2014 | Peters et al. |
| 2014/0249478 A1 | 9/2014 | Bierman et al. |
| 2014/0276542 A1 | 9/2014 | Ciccone |
| 2014/0276544 A1 | 9/2014 | Aviles |
| 2014/0276658 A1 | 9/2014 | Ward |
| 2014/0303574 A1* | 10/2014 | Knutson ............ A61K 31/4439 604/307 |
| 2014/0343501 A1 | 11/2014 | Bierman et al. |
| 2015/0008674 A1 | 3/2015 | Karim et al. |
| 2015/0088076 A1 | 3/2015 | Andino |
| 2015/0112270 A1 | 4/2015 | Smith et al. |
| 2015/0133891 A1 | 5/2015 | Rosenhan |
| 2015/0022428 A1 | 8/2015 | Teh et al. |
| 2015/0224285 A1 | 8/2015 | Howell et al. |
| 2015/0026580 A1 | 9/2015 | Bierman et al. |
| 2015/0367102 A1 | 12/2015 | Andino et al. |
| 2016/0008577 A1 | 1/2016 | Wright et al. |
| 2016/0015932 A1 | 1/2016 | Catudal |
| 2016/0067451 A1 | 3/2016 | Kyvik et al. |
| 2016/0018455 A1 | 6/2016 | Rosenberg et al. |
| 2016/0019345 A1 | 7/2016 | Hanson et al. |
| 2016/0020685 A1 | 7/2016 | Mitchell et al. |
| 2016/0031778 A1 | 11/2016 | Friedrich |
| 2017/0004313 A1 | 2/2017 | Jones et al. |
| 2017/0043131 A1 | 2/2017 | Ciccone et al. |
| 2017/0216556 A1 | 8/2017 | Bierman et al. |
| 2017/0296788 A1 | 10/2017 | Andino et al. |
| 2017/0296789 A1 | 10/2017 | Andino et al. |
| 2017/0326340 A1* | 11/2017 | Howell ................. A61M 25/02 |
| 2019/0002476 A1 | 8/2019 | Bracken et al. |
| 2020/0000305 A1 | 1/2020 | Andino et al. |

FOREIGN PATENT DOCUMENTS

| | | |
|---|---|---|
| WO | 9610435 A1 | 4/1996 |
| WO | 1997/005920 A1 | 2/1997 |
| WO | 9715337 A1 | 5/1997 |
| WO | 9715342 A1 | 5/1997 |
| WO | 1998/032481 A1 | 7/1998 |
| WO | 9853872 A1 | 12/1998 |
| WO | 1999/020334 A1 | 4/1999 |
| WO | 1999/025399 A1 | 5/1999 |
| WO | 9955409 A1 | 11/1999 |
| WO | 2000/010637 A1 | 3/2000 |
| WO | 2001/062328 A1 | 8/2001 |
| WO | 2001/068180 A1 | 9/2001 |
| WO | 01/91847 A2 | 12/2001 |
| WO | 2002/011786 A2 | 2/2002 |
| WO | 2002/056958 A2 | 7/2002 |
| WO | 2003/092781 A2 | 11/2003 |
| WO | 2004016309 A2 | 2/2004 |
| WO | 2004/030741 A2 | 4/2004 |
| WO | 2005/081882 A2 | 9/2005 |
| WO | 06087755 A1 | 8/2006 |
| WO | 2006/113620 A2 | 10/2006 |
| WO | 2007/011596 A2 | 1/2007 |
| WO | 2007/035605 A2 | 3/2007 |
| WO | 2007024900 A2 | 3/2007 |
| WO | 2007028007 A2 | 3/2007 |
| WO | 2007/075491 A2 | 7/2007 |
| WO | 2007/082093 A2 | 7/2007 |
| WO | 2007117655 A2 | 10/2007 |
| WO | 2008051810 A2 | 5/2008 |
| WO | 2008/116119 A2 | 9/2008 |
| WO | 2009/003137 A1 | 12/2008 |
| WO | 2008151047 A1 | 12/2008 |
| WO | 09/032008 A2 | 3/2009 |
| WO | 2009/035450 A1 | 3/2009 |
| WO | 2009055739 A1 | 4/2009 |
| WO | 2010/002393 A1 | 1/2010 |
| WO | 2010/016837 A1 | 2/2010 |
| WO | 2010/033109 A1 | 3/2010 |
| WO | 2010/033858 A1 | 3/2010 |
| WO | 2010102153 A1 | 9/2010 |
| WO | 10/132837 A1 | 11/2010 |
| WO | 2010/132843 A1 | 11/2010 |
| WO | 2011025478 A1 | 3/2011 |
| WO | 2011/044256 A1 | 4/2011 |
| WO | 2011/044259 A1 | 4/2011 |
| WO | 2011/044293 A1 | 4/2011 |
| WO | 2011/109542 A1 | 9/2011 |
| WO | 2012/015440 A1 | 2/2012 |
| WO | 2014/149668 A1 | 9/2014 |
| WO | 16164598 A2 | 10/2016 |

OTHER PUBLICATIONS

U.S. Appl. No. 15/594,507, filed May 12, 2017 Final Office Action dated Jun. 29, 2020.
PCT/US2017/032558 filed May 12, 2017 International Search Report and Written Opinion dated Aug. 3, 2017.
U.S. Appl. No. 15/594,507, filed May 12, 2017 Advisory Action dated Feb. 4, 2020.
U.S. Appl. No. 15/594,507, filed May 12, 2017 Final Office Action dated Nov. 20, 2019.
U.S. Appl. No. 15/594,507, filed May 12, 2017 Non-Final Office Action dated Apr. 17, 2020.
U.S. Appl. No. 15/594,507, filed May 12, 2017 Non-Final Office Action dated Jun. 6, 2019.
U.S. Appl. No. 15/594,507, filed May 12, 2017 Restriction Requirement dated Mar. 22, 2019.
U.S. Appl. No. 15/594,507, filed May 12, 2017 Final Office Action dated Jun. 29, 2022.

* cited by examiner

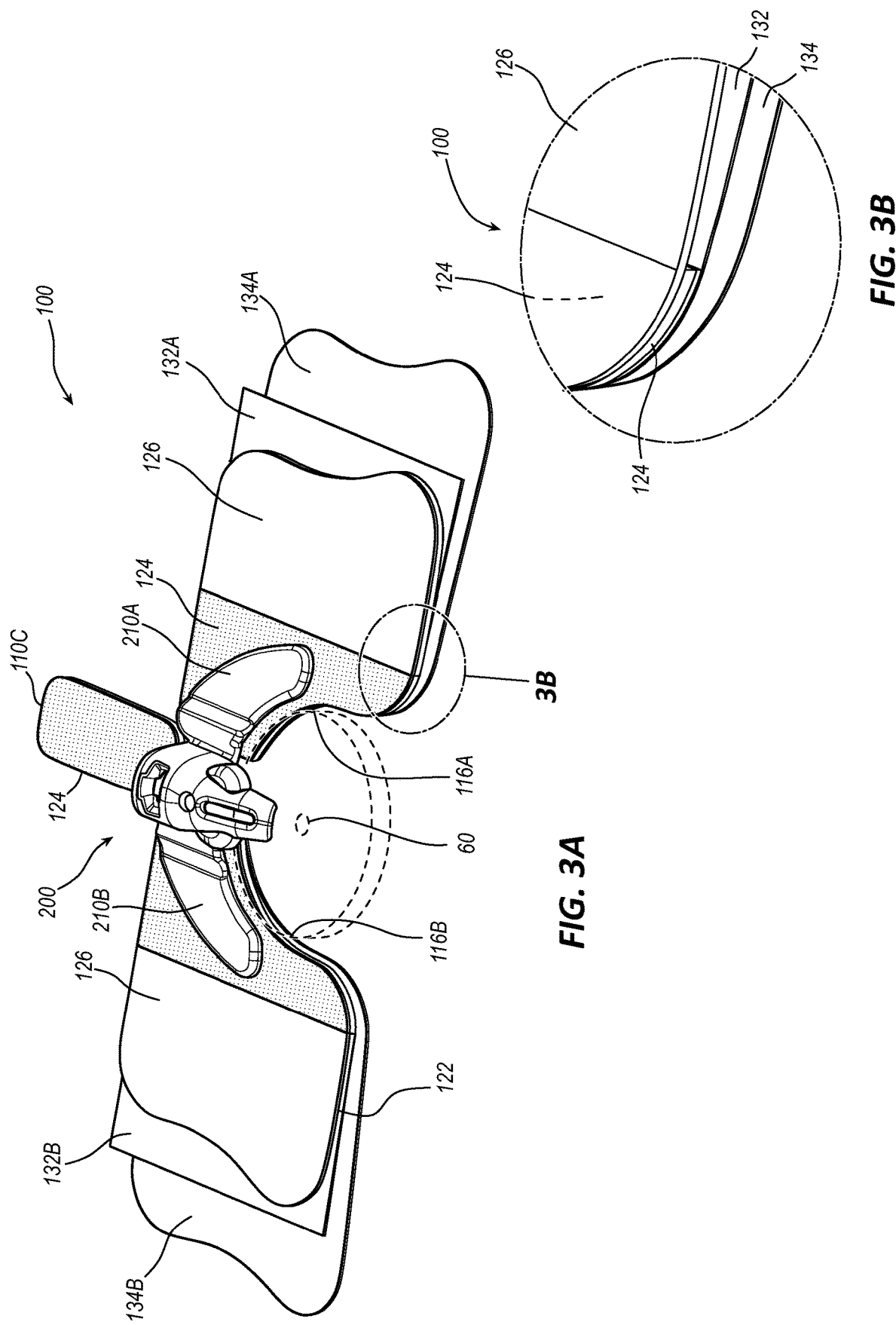

CATHETER SECUREMENT DEVICE INCLUDING EXTENDED ANCHOR PAD AND RELEASE LINER CLASPING FEATURES

PRIORITY

This application claims the benefit of priority to U.S. Provisional Application No. 62/835,312, filed Apr. 17, 2019, which is incorporated by reference in its entirety into this application.

SUMMARY

Briefly summarized, embodiments of the present invention are directed to a securement device configured to secure an external portion of a medical device, e.g. a catheter assembly, to a skin surface of a patient. The securement device includes a retainer that is employed to securely but removably retain an external portion of the catheter assembly in place. In one embodiment, the retainer is attached to an anchor pad such as an adhesive pad that adhesively attaches to the skin surface. As used herein the securement device can also be referred to herein as a catheter retainer system or catheter retainer assembly.

In an embodiment, the retainer includes a body defining a channel and at least one mounting wing, or footing, extending from the body. The mounting wing is configured to extend to, or distally of, the insertion site to stabilize the insertion site and adjacent skin surface, relative to the securement device and prevent rocking or pistoning. The mounting wing further includes channels configured to impart malleable properties on the mounting wing so that the wing can be shaped to fit different portions of the patient. The retainer further includes various locking and anti-rotational to guide the catheter into position within the retainer and further prevent rocking or pistoning. The securement device also includes a protective pad to inhibit abrasions from a medical line, or the like, coupled to the catheter. The securement device further includes a clasping feature to hold a liner in a retracted position to prevent obstructing ingress/egress of the catheter to/from the retainer.

Disclosed herein is a securement device for stabilizing an elongate medical article on a skin surface of a patient including, a retainer having a retainer body defining a channel aligned with a central axis of the securement device, and configured to receive a portion of the elongate medical article, and a mounting wing supporting the retainer body, an anchor pad supporting the mounting wing, including an adhesive layer disposed on a portion of a lower surface of the anchor pad, and defining an outer edge and an inner edge disposed laterally opposite the outer edge, and a release liner including a first portion disposed on the adhesive layer and extending from the outer edge to the inner edge, and a second portion coupled to the first portion along the inner edge and extending from the inner edge to the outer edge, the release liner including a clasping feature configured to releasably secure the second portion to the first portion proximate the outer edge.

In some embodiments, the first portion is disposed between the second portion and the adhesive layer, the second portion extends laterally outward from the outer edge to define a pull tab. The clasping feature includes a flap die cut into the second portion and configured to releasably secure the second portion to one of the first portion of the release liner or the anchor pad. The clasping feature includes an aperture disposed in the first portion of the release liner, and configured to allow an upper surface of the second portion to contact the adhesive layer, releasably securing the second portion thereto. The anchor pad includes a fabric upper layer, and a central foam layer extending over a portion of the anchor pad and disposed between the fabric upper layer and the adhesive layer.

In some embodiments, the securement device further includes a protective pad extending from a proximal edge of the anchor pad, aligned with the central axis of the securement device and disposed between the elongate medical device and the skin surface of the patient. The protective pad includes a central foam layer and a release agent disposed on an upper surface thereof, and wherein the protective pad is configured to mitigate abrasions to the skin surface caused by the elongate medical device. The protective pad further includes a tear line dispose between the protective pad and the anchor pad and configured to selectively release the protective pad from the anchor pad. The elongate medical device is a midline catheter, a dialysis catheter, a Central Venous Catheter ("CVC"), a Peripherally Inserted Central Catheter ("PICC"), a Peripherally Inserted Venous catheters ("PIV"), a Foley catheter, a urinary catheter, a feeding tube, or a balloon catheter.

Also disclosed is a securement device for stabilizing an external portion of a catheter assembly after insertion of an internal portion of the catheter assembly into a body of a patient via a catheter insertion site, the securement device including, a retainer body defining a channel, a first mounting wing and a second mounting wing supporting the retainer body, a distal edge of the first mounting wing and the second mounting wing extending distally beyond the catheter insertion site, a first anchor pad and a second anchor pad, the first anchor pad supporting the first mounting wing, the second anchor pad supporting the second mounting wing, and a protective pad disposed proximally of the first anchor pad and the second anchor and disposed between the external portion of the catheter assembly and a skin surface of the patient.

In some embodiments, the first mounting wing and the first anchor pad adheres to a first portion of the skin, surface adjacent the insertion site, and the second mounting wing and the second anchor pad adheres to a second portion of the skin surface adjacent the insertion site, opposite the skin surface first portion, the first mounting wing and the second mounting wing stabilizing the insertion site, disposed therebetween, relative to the catheter assembly. One of the first mounting wing or the second mounting wing includes a channel configured to impart malleable characteristics on the mounting wing. A thickness of the mounting wing within the channel is between 0.010 in. and 0.020 in. The retainer body, the first mounting wing and the second mounting wing are configured to mitigate rocking or pistoning of the catheter assembly. A nose portion of the retainer body includes a cutaway portion configured to retain an antimicrobial disc between the nose portion and the insertion site.

In some embodiments, the nose portion is configured to deflect a strain relief of the catheter assembly at a predetermined angle and an axis of the external portion of the catheter assembly extends substantially parallel to the skin surface of the patient. The first mounting wing and the second mounting wing are configured to receive the antimicrobial disc therebetween. In some embodiments, the securement device further includes an anti-rotation feature configured to inhibit rotation of catheter assembly relative to the retainer and to align the catheter assembly with the retainer. The anti-rotation feature includes one of a pocket, alignment channel, or a locking window configured to engage one of a nub, alignment ring, or locking tab disposed on the catheter assembly. The retainer body is formed of one of a transparent, translucent, or semi-translucent material, and is configured to allow a clinician to view a position of the catheter assembly therebelow. The retainer body includes a viewing window communicating between the channel and an outer surface thereof and configured to allow a user to observe the external portion of the catheter assembly disposed therebelow. The catheter assembly includes a colored portion configured to align with the viewing window to indicate that the external portion of the catheter assembly is correctly aligned with the retainer body. The protective pad is configured to inhibit trauma to the skin surface from the external portion of the catheter assembly.

Also disclosed is a method of securing a catheter assembly including, providing a securement device having, a retainer body defining a channel configured to receive at least a portion of the catheter assembly, a mounting wing supporting the retainer body, an anchor pad coupled to the mounting wing and including an adhesive layer disposed on a lower surface thereof, and a release liner including a first portion disposed on the adhesive layer, and a second portion integrally formed with the first portion along a first edge and extending laterally outward to a second edge, opposite the first edge, receiving the portion of the catheter assembly within the channel, positioning a bottom surface of the securement device against a skin surface of a patient, urging the second portion laterally outward, peeling the release liner first portion away from the adhesive layer from the first edge to the second edge, and adhering the retainer to the skin surface of the patient.

In some embodiments, the release liner second portion further includes a clasping feature configured to releasably secure the release liner second portion to the release line first portion proximate the second edge. The clasping feature is a flap that is die cut into the release liner second portion. The clasping feature is an aperture disposed in the release liner first portion that allows a portion of the adhesive layer to contact the release liner second portion. The second portion extends laterally outward beyond the second edge to define a pull tab. In some embodiments, the method further includes positioning a protective pad between a second portion of the catheter assembly and the skin surface of the patient, the protective pad extending proximally from a proximal edge of the anchor pad and releasably coupled thereto. In some embodiments, the method further includes sliding an anti-microbial disc longitudinally proximally between a nose portion of the retainer body and a skin surface, the nose portion angled to impinge on the disc and retain the disc therebetween. In some embodiments, the method further includes bending the mounting wing from a first position to a second position, the mounting wing including a channel configured to impart malleable characteristics so that the mounting wing remains in the second position until repositioned.

These and other features of embodiments of the present invention will become more fully apparent from the following description and appended claims, or may be learned by the practice of embodiments of the invention as set forth hereinafter.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 3A shows a front perspective view of a catheter securement device, in accordance with embodiments disclosed herein.

FIG. 3B shows close up detail of an anchor pad of the catheter securement device of FIG. 3A, in accordance with embodiments disclosed herein.

DETAILED DESCRIPTION

Figure 1A:
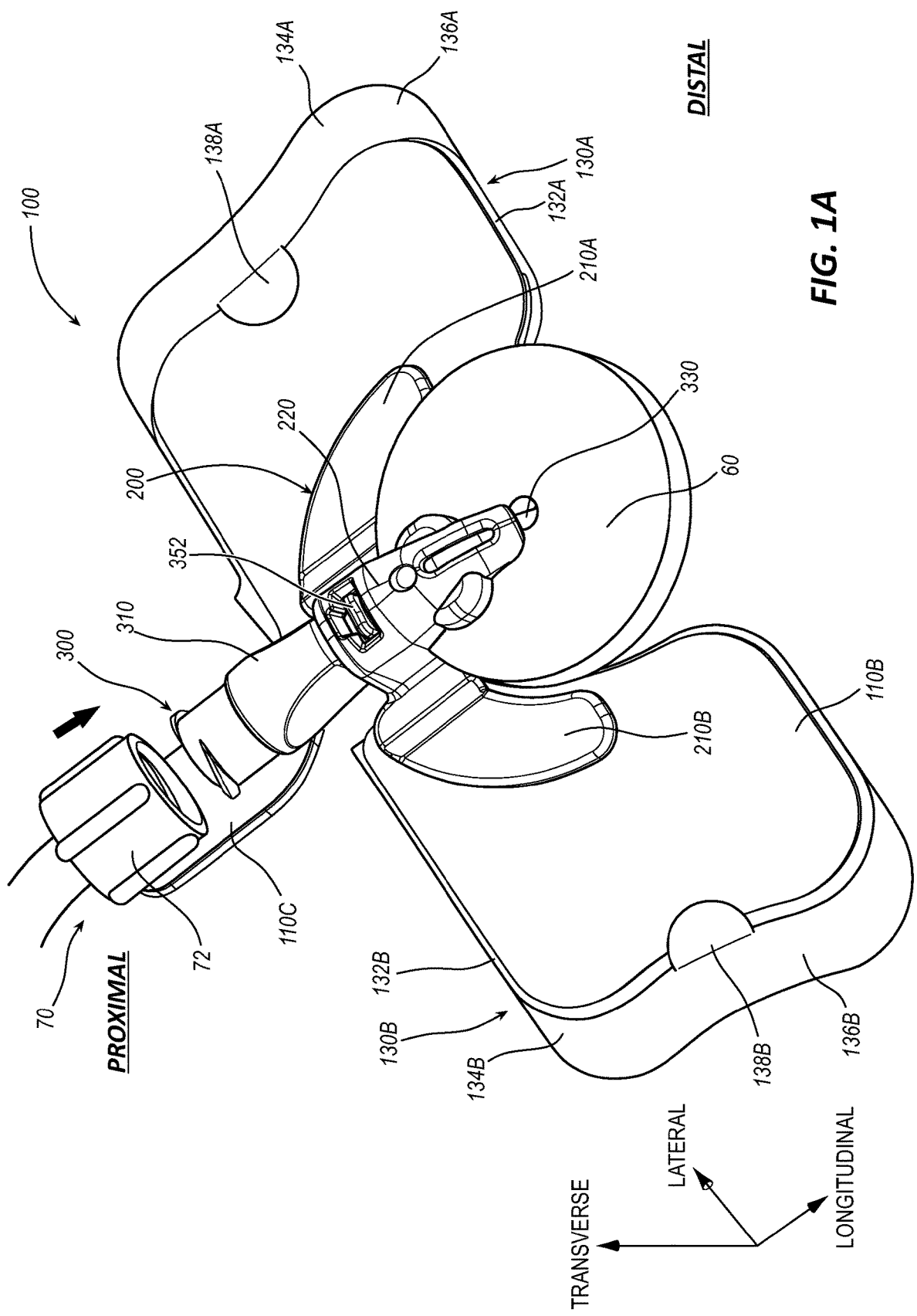
FIG. 1A shows a front perspective view of a catheter securement device, in accordance with embodiments disclosed herein.

Reference will now be made to figures wherein like structures will be provided with like reference designations. It is understood that the drawings are diagrammatic and schematic representations of exemplary embodiments of the present invention, and are neither limiting nor necessarily drawn to scale. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise. Also, the words "including," "has," and "having," as used herein, including the claims, shall have the same meaning as the word "comprising."

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

To assist in the description of the securement system, the following coordinate terms are used (for example, see FIG. 1A). A "longitudinal axis" is generally parallel to the axis of a channel of the retainer, through which the medical article extends. A "lateral axis" is normal to the longitudinal axis. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The term "axial" as used herein refers to the axis of the channel, and therefore is substantially synonymous with the term "longitudinal" as used herein. As used herein, the terms "yaw," "pitch," and "roll" are used to in relation to movement, about a center point of the device, rotating about the transverse, lateral, and longitudinal axes respectively.

Unless defined otherwise, all technical and scientific terms used herein have the same meaning as commonly understood by those of ordinary skill in the art.

Embodiments of the present invention are generally directed to a securement device that is configured to secure an external portion of a catheter assembly to the skin surface of a patient after an internal portion of the catheter assembly has been placed in the patient to establish vascular access, or for some other suitable purpose. The securement device includes a catheter retainer that is employed to securely but removably retain the external portion of the catheter assembly in place. In one embodiment, the catheter retainer is attached to an anchor pad, or base, such as an adhesive pad that adhesively attaches to the skin surface, to form the securement device, also referred to herein as a catheter retainer system or catheter retainer assembly. It is appreciated that, though the discussion to follow focuses on a midline catheter, catheters and other tubular or elongate medical devices that are configured for attachment or may be attached to a skin surface of the patient may also benefit from the teachings herein, including dialysis catheters, Central Venous Catheter ("CVC"), Peripherally Inserted Central Catheter ("PICC"), Peripheral Intravenous catheter ("PIV"), Foley and urinary catheters, feeding tubes, balloon catheters, etc. In one embodiment, the catheter securement device includes support wings, or mounting wings, which extend distally beyond the insertion site to reduce rocking or pistoning of the catheter, both internally and externally of the insertion site. The mounting wings can further include channels to facilitate shaping of the support wing to different curvatures of a skin surface, depending on the location of the securement device. In an embodiment, a release liner disposed on a lower adhesive surface of the anchor pad includes clasping features that secure to lateral edges of the device. This prevents portions of the release liner from obstructing ingress/egress of the catheter to/from the retainer. Embodiments herein further describe additional aspects of the catheter securement device.

FIGS. 1A-3E depict details of various embodiments of a catheter securement device ("securement device") 100.

Figure 1B:
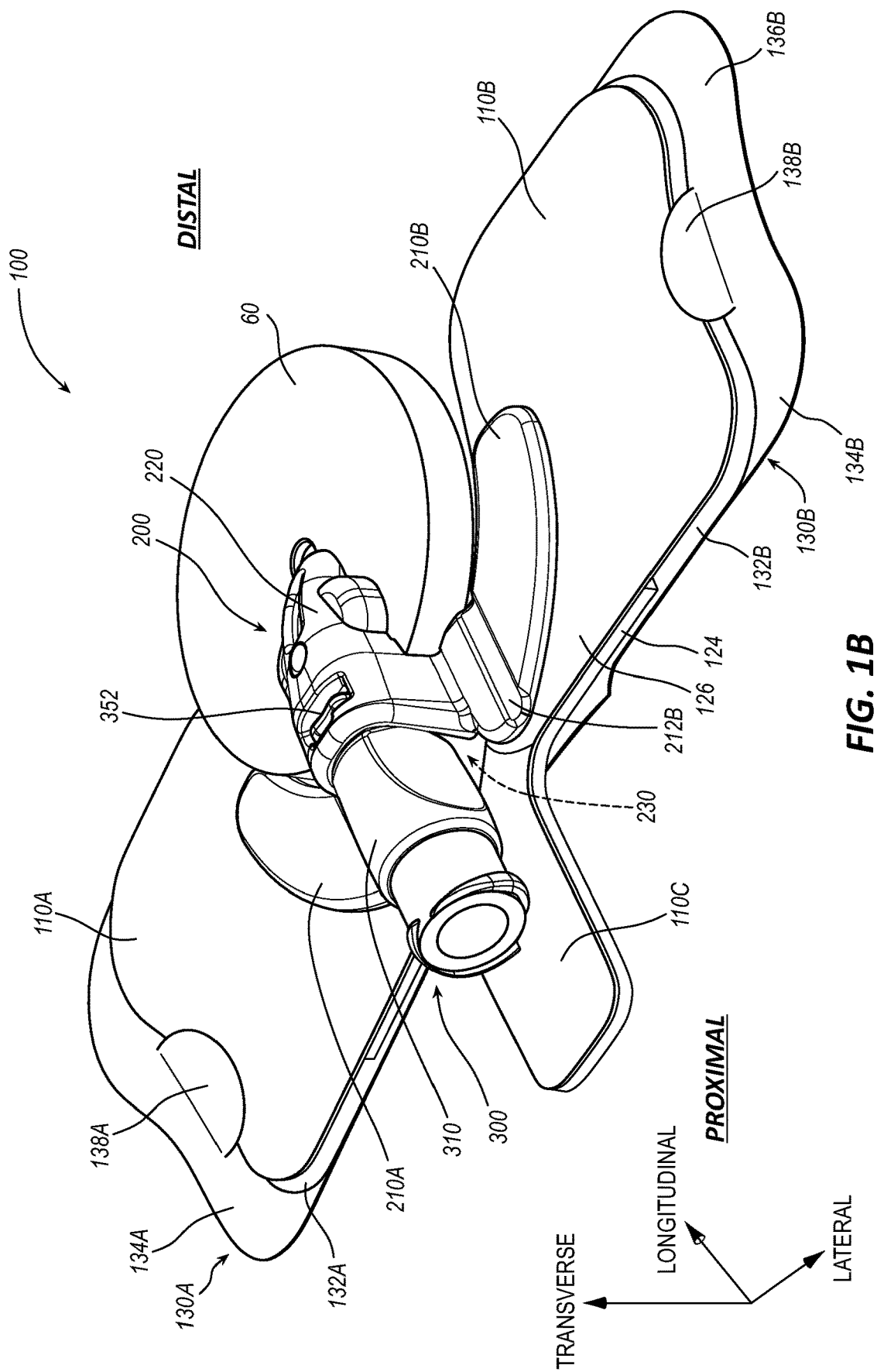
FIG. 1B shows a rear perspective view of the catheter securement device of FIG. 1A, in accordance with embodiments disclosed herein.
Figure 1C:
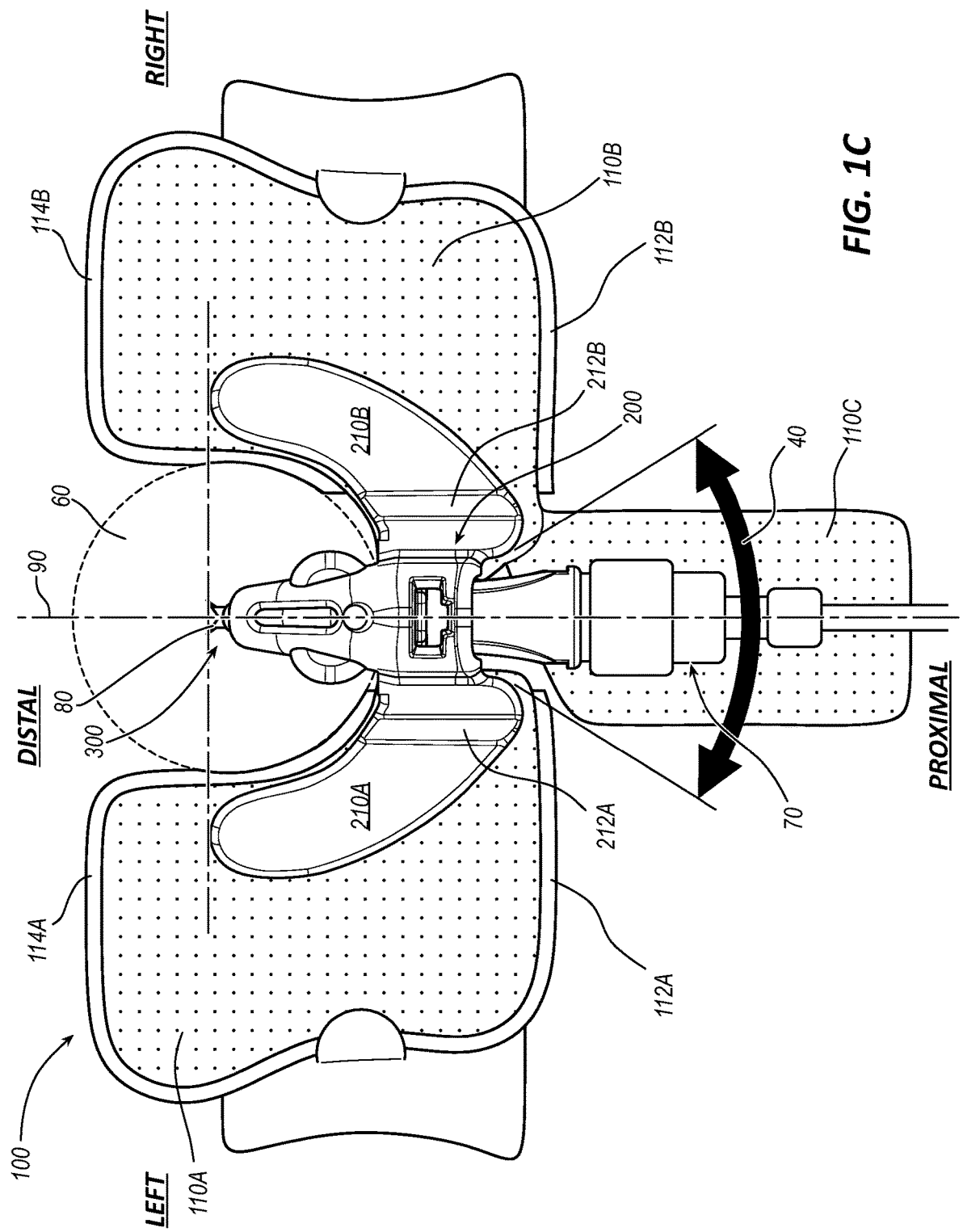
FIG. 1C shows a plan view of the catheter securement device of FIG. 1A, in accordance with embodiments disclosed herein.

As shown in FIGS. 1A-1C, the securement device 100 can include an anchor pad 110, such as a left anchor pad 110A and a right anchor pad 110B, a protective pad 110C, and a retainer 200. The retainer 200 can be designed to retain a portion of an elongate medical article, for example a catheter system ("catheter") 300, extension set, medical I.V. line, combinations thereof, or the like. The catheter system 300 generally comprises a catheter hub 310, which supports an elongate catheter tube 320 extending distally from the catheter hub 310. The catheter 300 can further include a strain relief portion 330 that further supports the catheter tube 320. A proximal end of the catheter hub 310 can be coupled to a medical line, such as an extension set 70, using a spin nut 72, luer lock (not shown), or similar suitable connection. The catheter 300 includes a lumen extending from a proximal end to a distal end, and provides fluid communication between the medical line and a vasculature of a patient.

In an embodiment, the anchor pad 110 comprises a central foam portion 124 and a fabric overlap 126 and can include an adhesive layer disposed on a bottom surface thereof. The adhesive layer can be covered by a protective release liner 130, for example a left release liner 130A and a right release liner 130B. Each release liner 130 can include a first portion 132, a second portion 134, a pull tab 136, a clasping feature 138, or combinations thereof, as described in more detail herein.

The retainer 200 includes a body portion 220 supported by at least one mounting wing 210, such as a left mounting wing 210A and a right mounting wing 210B, as discussed in more detail herein. The body portion 220 defines a central channel 230 that is designed to retain at least a portion of the elongate medical article, such as catheter hub 310, although it will be appreciated that any portion of the catheter 300, extension set 70, spin nut 72, combinations thereof, or the like, can be retained therein. The channel 230 can inhibit at least lateral and transverse movement of the catheter hub 310, further the retainer 200 can include one or more abutments, or the like, to inhibit longitudinal movement of the catheter hub 310, relative to the device 100. The retainer 200 can further include an elongate opening 232, extending longitudinally and communicating with the channel 230 to allow ingress/egress of the catheter hub 310. As shown, e.g. FIG. 2H, the opening 232 can be disposed on an underside of the retainer, although in an embodiment the opening 232 can be disposed on a side surface or an upper surface of the retainer 200. In an embodiment, the retainer 200 can further include various straps, latches, clasps, or the like to further secure the medical article within the retainer without departing from the spirit of the invention. In an embodiment, retainer 200 can be formed of a polycarbonate plastic, although other materials displaying similar suitable characteristics are also contemplated.

As shown for example in FIG. 1C, in an embodiment, a distal edge of the mounting wing 210, anchor pad 110, or combinations thereof, extends distally of a catheter insertion point 80. As such, the left mounting wing 210A and the right mounting wing 210B, which are secured to the left and right anchor pads 110A, 110B respectively, are secured to the skin surface that surrounds the insertion site 80. The mounting wings 210A, 210B, thereby stabilize the insertion site 80, and surrounding skin surface 50 relative to the securement device 100 and prevent any "rocking" or "pistoning" of the catheter 300, as described in more detail herein.

Figure 1D:
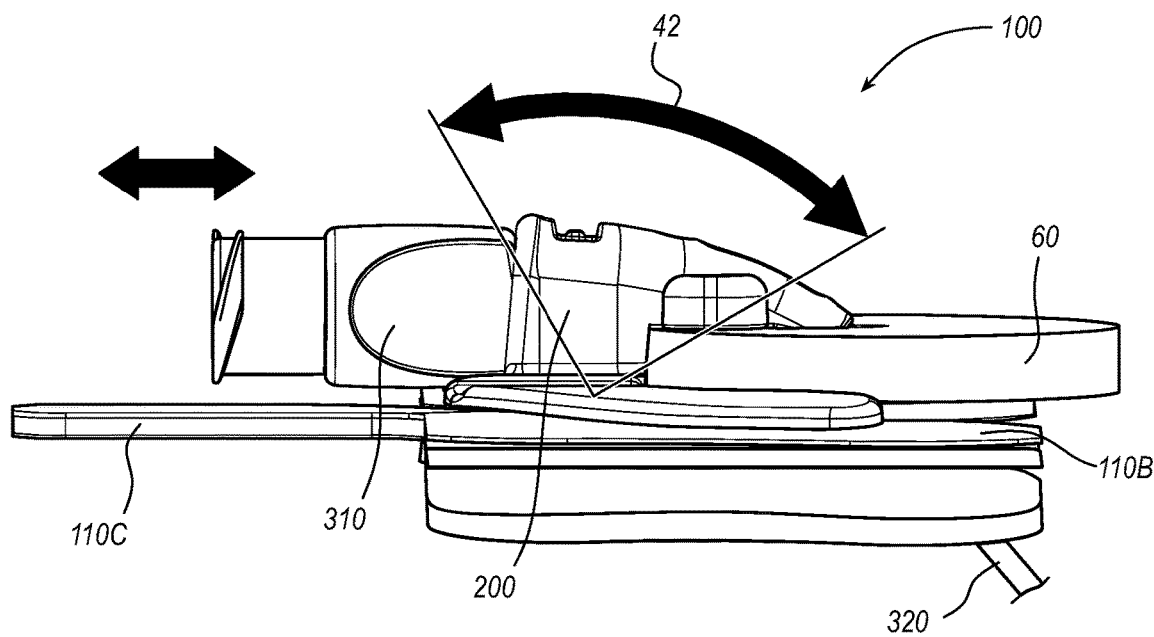
FIG. 1D shows a side-view of the securement device of FIG. 1A, in accordance with embodiments disclosed herein.

As shown in FIG. 1C, the configuration of the mounting wings 210 provides little or no yaw movement 40 about the center point of the securement device 100 when the securement device is adhered to the skin. Further, the configurations of the mounting wings 210A, 201B provide little or no yaw movement relative to each other. Similarly, as shown in FIG. 1D, the configuration of the mounting wings 210A, 210B, provides little or no pitch movement 42 of the securement device 100 when adhered to the skin. As such, the insertion site 80 secured between the left mounting wing 210A and right mounting wing 210B is stabilized relative to the securement device 100 and prevents the catheter from "rocking," i.e. rotating about a center point of the securement device 100 about the transverse axis (FIG. 1C) or about the lateral axis (FIG. 1D). For example, when a medical line, or the like, is attached to a catheter hub 310 that is retained by the securement device 100, pressure is applied as the clinician presses and twists a spin nut 72 into place. This pressure can be a longitudinal distal force that causes the catheter to pivot about the retainer body 220 through a horizontal plane and/or longitudinally vertical plane. These forces can cause the catheter 300 to move relative to the insertion site 80 causing kinking of the catheter tube 320 either internally or externally of the insertion site 80. Kinking of the catheter tube 320 can obstruct a fluid flow therethrough and can cause discomfort to the patient.

Figure 1E:
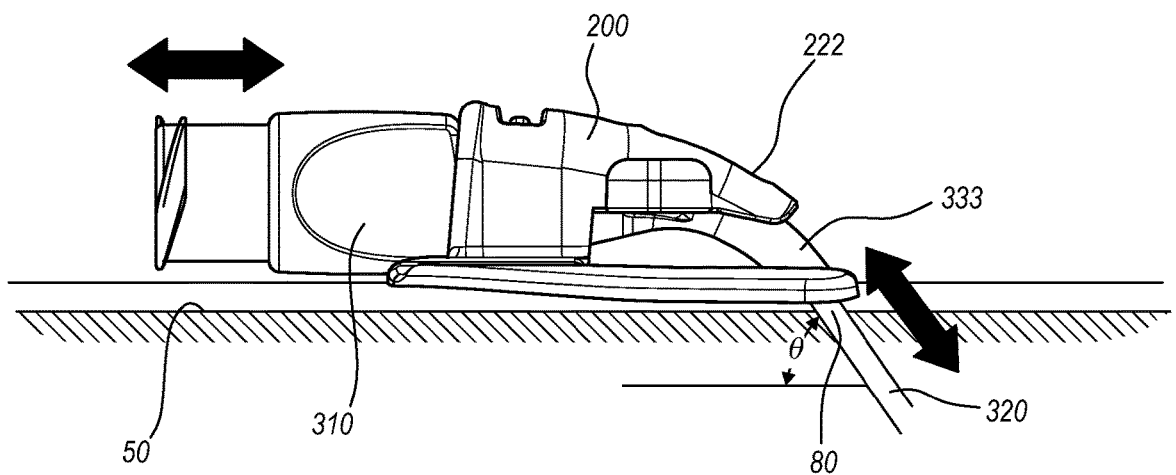
FIG. 1E shows a side-view of the retainer of the securement device of FIG. 1A, in accordance with embodiments disclosed herein.

Further, the configuration of the mounting wings 210 stabilizing the insertion site 80 relative to the securement device 100 also prevents "pistoning" of the catheter 300. For example, as shown in FIG. 1E, the configuration of the mounting wings 210 prevents any movement of catheter along a longitudinal axis, relative to the insertion site 80. As such, the securement device prevents any "Z-kinking" of the catheter tube 320 caused by compression of the catheter tube 320 between the retainer 200 and the insertion site 80. Such kinking can disrupt fluid flow and cause discomfort, as described herein. In an embodiment, the configuration of the mounting wings 210A, 210B, prevents "pistoning" movement of the catheter tube 320 in and out of the insertion site 80. This prevents the introduction of microbes, bacteria, and the like, into the insertion site 80, and mitigates infection.

As shown in FIGS. 1A-1D and 1F, in an embodiment and as discussed in more detail herein, the retainer body 220 and mounting wings 210A, 210B are configured to receive and retain an antimicrobial disc ("disc") 60, for example a GuardIVa® Hemostatic pad, or similar anti-microbial hemostatic IV dressing. The disc 60 defines a substantially flattened cylinder with a circular outer perimeter 64. The disc 60 can define a substantially 1 inch diameter although greater or lesser dimensions are also contemplated. The disc 60 includes a central aperture 66 extending from a top surface to a bottom surface. The disc further includes a slit 62 communicating between the outer perimeter 64 and the central aperture 66. The slit 62 is configured to allow a portion of the catheter 300, e.g. catheter tube 320, strain relief 330, and the like, to pass therethrough to be received within the central aperture 66. The disc 60 can be secured in place between a nose portion 222 of the retainer 200 and the skin surface 50 of the patient. Further details of which can be found in US 2017/0326340 which is incorporated by reference in its entirety herein.

Figure 1F:
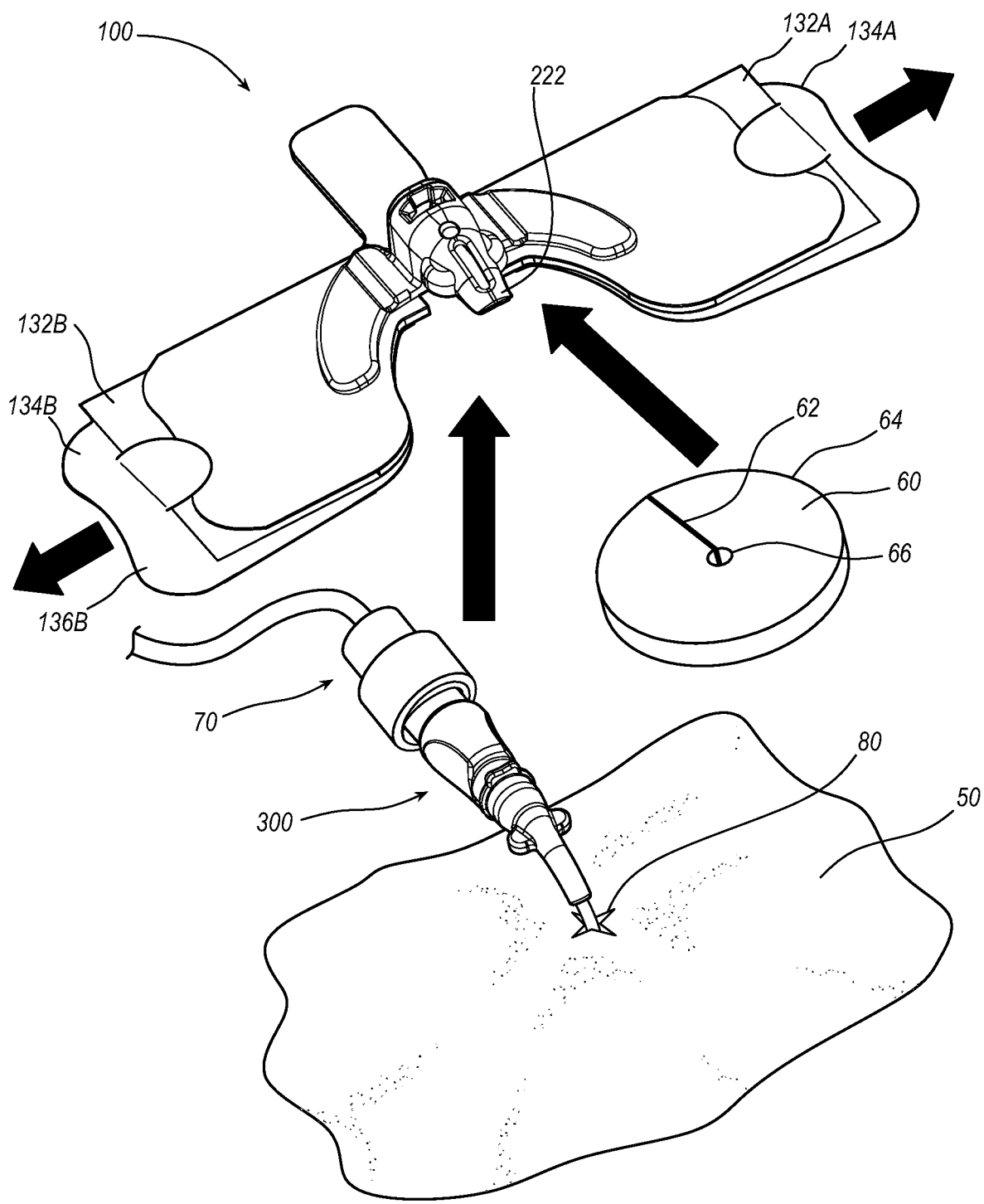
FIG. 1F shows an exploded view the catheter securement device of FIG. 1A, in accordance with embodiments disclosed herein.

FIG. 1F depicts an exploded view of the catheter securement device 100, the catheter 300 and the antimicrobial disc 60. In an exemplary method of use, a distal portion of a catheter 300 is inserted into a patient to access a vasculature thereof. The securement device 100, including the retainer 200, can then be lowered onto an external portion of the catheter 300, e.g. the catheter hub 310 and strain relief 330, to stabilize the external portion against a skin surface of the patient. The protective pad 110C is positioned between the catheter hub 330 and the skin surface of the patient to inhibit abrasions. The insertion site 80 can be positioned between the distal portions of mounting wings 210 to stabilize the insertions site 80, and surrounding skin, relative to the securement device 100. The release liner 130 can then be removed by pulling on pull tab 136 in a lateral outward direction. Pulling the pull tab 136 as such peels the first portion 132 of the release liner 130 away from a laterally inner edge and allows the adhesive layer 128 to adhere to a skin surface of the patient, as described in more detail herein. An anti-microbial disc 60 can then be positioned over the insertion site 80 by sliding the disc 60 longitudinally and proximally. The portion of catheter tube 320 and strain relief 330, disposed externally to the patient, can pass through the slit 66 and into the central aperture 66 and held in place by the nose portion 222 and mounting wings 210A, 210B.

FIGS. 2A-2H show various details of an exemplary retainer 200 of the securement device 100.

Mounting Wings

The retainer body 220 is supported by mounting wings 210, such as left and right mounting wing 210A, 210B. For example, left mounting wing 210A is coupled to a lower left portion of retainer body 220 and right mounting wing 210B is coupled to a lower right portion of the retainer body 220. Each of the mounting wings 210A, 210B extend laterally outward and longitudinally distally from a central axis 90 of the retainer body 220 so that, in an embodiment, a distal most portion of the mounting wing 210A, 210B extends beyond a distal end of the retainer body 220. In an embodiment, as shown in FIG. 2B, each of the mounting wings 210A, 210B can define a curved outer perimeter, or "footprint," when viewed from a plan view. It will be appreciated however that the shape of the outer perimeter of the mounting wings 210, can include angular, or various other shapes, and still fall within the scope of the present invention. Further, as shown in FIG. 2B, mounting wing 210A is substantially a "mirror image" shape of mounting wing 210B. However, in an embodiment, the left and right mounting wings 210A, 210B can be asymmetrical, i.e. of differing size and shape from each other.

Each of the left and right mounting wings 210A, 210B are coupled with a left and right anchor pads 110A, 110B, respectively. In an embodiment, at least a portion of the lower surface of the mounting wing 210 is attached to an upper surface of the anchor pad 110. The mounting wings 210 can be coupled to the anchor pads 110 using adhesive, bonding, welding, or similar suitable techniques. As shown for example in FIGS. 1A, 2H, 3C-3D, anchor pads 110A, 110B are in a laterally spaced apart relationship to allow ingress/egress of the medical article therebetween, by way of an underside of the device 100. In an embodiment, left and right anchor pads 110A, 110B can be formed integrally, so as to form a single anchor pad 110. For example, where ingress/egress of the medical article to/from the retainer 200 is by way of an upper side thereof, a single anchor pad 110 can be provided.

Channels

Figure 2A:
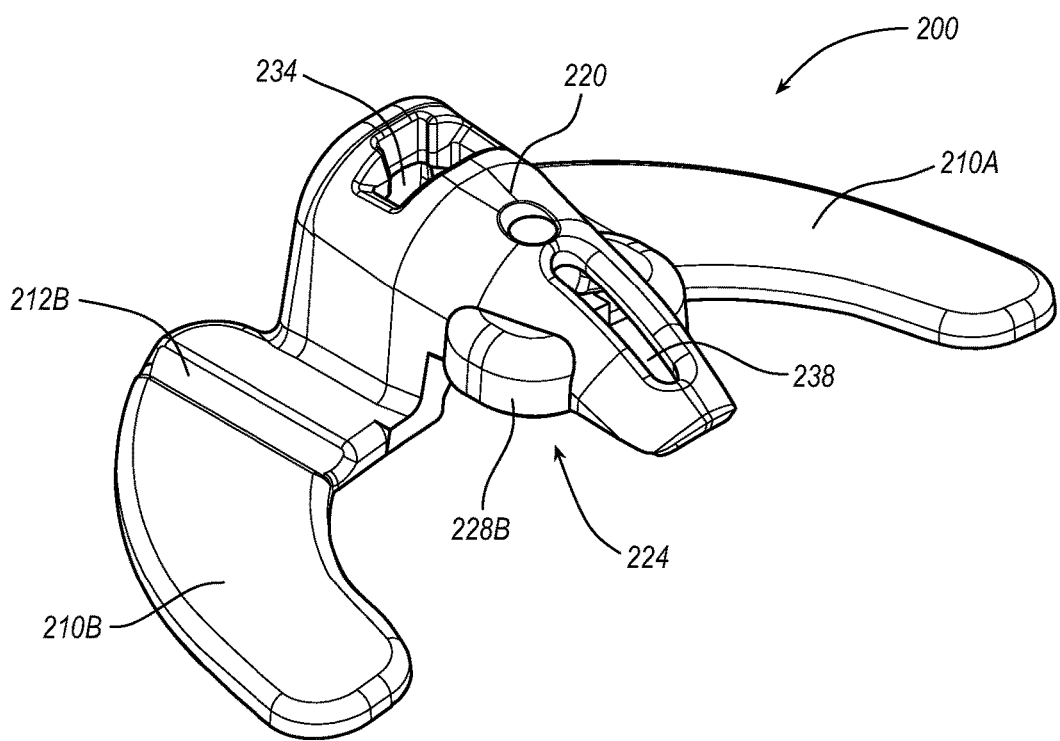
FIG. 2A shows a perspective view of a retainer, in accordance with embodiments disclosed herein.
Figure 2B:
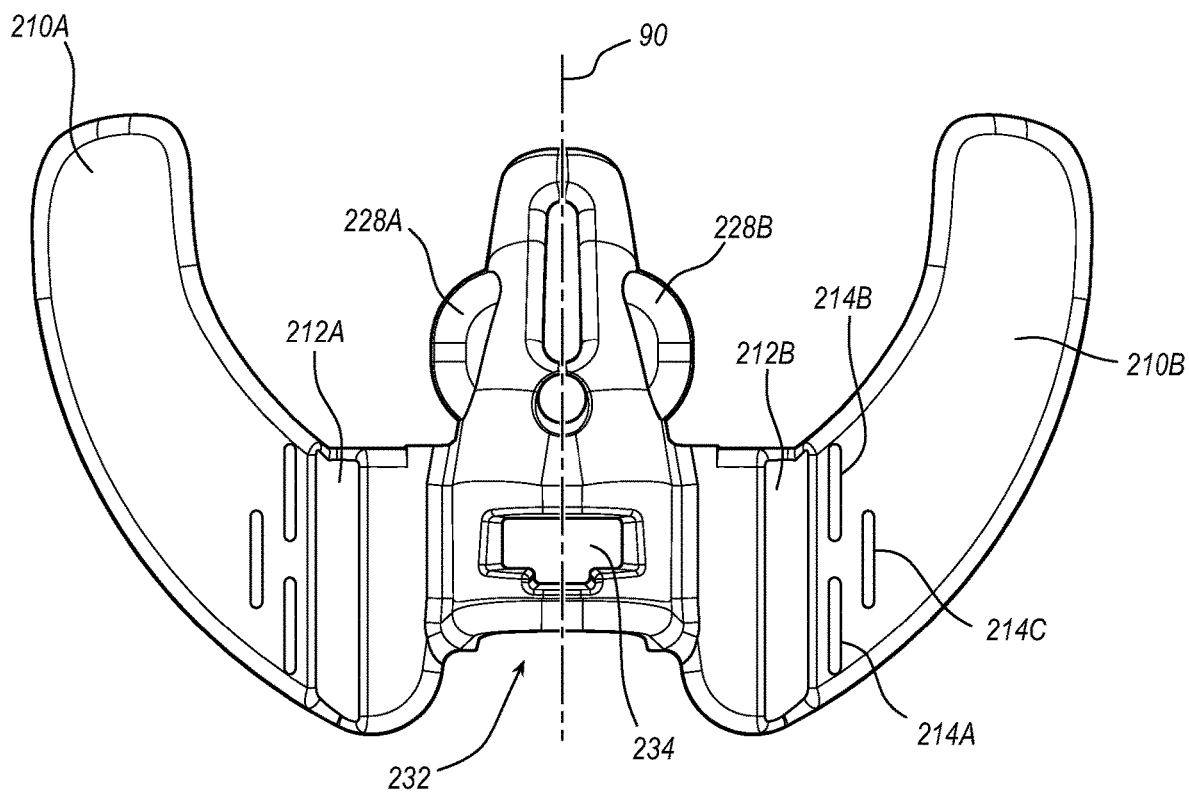
FIG. 2B shows a top-side plan view of a retainer, in accordance with embodiments disclosed herein.
Figure 2C:
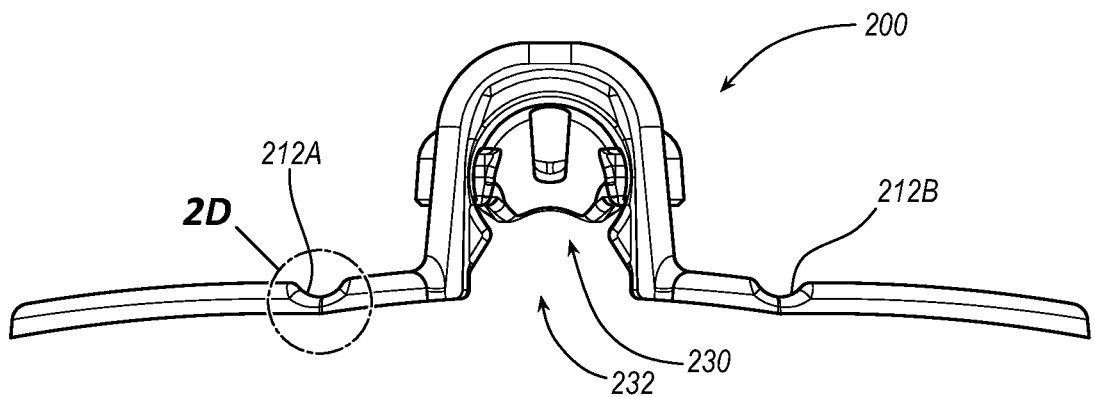
FIG. 2C shows a rear side view of a retainer, in accordance with embodiments disclosed herein.

As shown in FIGS. 2B-2C, in an embodiment, the mounting wings 210 can include a channel 212, for example a left channel 212A and a right channel 212B. The channel 212 extends longitudinally and can define a living hinge. The channel 212 extends from a proximal edge to a distal edge of the mounting wing and is laterally offset from a central axis 90 of the device 100. In an embodiment, the longitudinal axis of the channel 212 substantially aligns with an inner edge of the anchor pad 110, however other lateral positions on the mounting wing 210 are also contemplated.

In an embodiment, the channels 212 are dimensioned so as to allow the mounting wings 210 to be shaped to a predetermined angle and remain in place, thus imparting malleable characteristics on the mounting wings 210. As mentioned, the retainer 200 can be formed of a polycarbonate plastic. Channels 212, formed in the mounting wings 210, provide a portion of the wing that is of a reduced thickness. The reduced thickness of the mounting wing can reduce the elasticity of the mounting wing, to provide more malleable characteristics. This allows the wing to be shaped through a laterally vertical plane to a predetermined angle and remain at the predetermined angle until reshaped. As used herein, elastic characteristics are where the wing can deform when a force is applied and then return to its original shape when the force is removed. By contrast, malleable characteristics includes deformation when a force is applied but remain in the deformed shape when the force is removed.

In an embodiment, a thickness of the wing 210 within the channel 212, i.e. thickness (x), can be between 0.005 in. and 0.035 in. In an embodiment, the thickness (x) of the wing 210 within the channel 212 can be between 0.010 in. and 0.020 in. The thickness (x) is sufficient to reduce the elasticity of the wing to impart malleable characteristics on the mounting wing 210. Further, the thickness (x) is sufficient to maintain the position of the wing once shaped to a desired angle. In an embodiment, the channel 212 defines a V-shape or a U-shape cross section, although other cross-sectional shapes are also contemplated. In an embodiment, the lateral width and/or longitudinal length of the channels 212 can also vary to provide desired malleable characteristics. In an embodiment, the retainer is formed of a transparent or translucent polycarbonate material, as the mounting wing including the channel 212 is positioned from a first position to a second position, the polycarbonate material can yield and can turn white to indicate the wing has been shaped. In an embodiment, the malleable properties of the channel allows the mounting wing 210 to remain in the second position until repositioned.

Figure 2D:
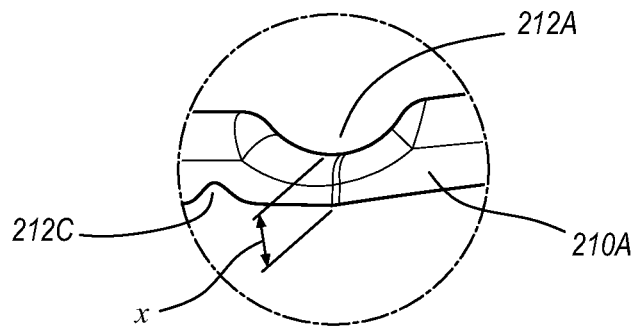
FIG. 2D shows close up detail of the retainer of FIG. 2C, in accordance with embodiments disclosed herein.

In an embodiment, the mounting wing 210 can include more than one channel 212. As shown in FIG. 2D, in an embodiment, a first left channel 212A is defined in an upper surface of the mounting wing 210, and a second left channel 212C is defined in a lower surface of the mounting wing 210. In an embodiment, a channel 212A on the upper surface and a channel 212C on the lower surface can be laterally aligned. In an embodiment, a channel 212A on the upper surface and a channel 212C on the lower surface can be laterally offset.

In an embodiment, as shown in FIG. 2B, a channel 214 only partially transects the mounting wing 210. For example, channel 214A extends distally from proximal edge of the mounting wing 210 to a point that is proximal of a distal edge of the mounting wing 210. Similarly, channel 214B extends proximally from distal edge of the mounting wing 210 to a point that is distal of a proximal edge. Channel 214C extends through a mid-point of the mounting wing. Varying numbers and combinations of channels 214A-214C can provide a "lattice" of channels. Further, varying numbers and combinations of channels 212A-212C, 214A-214C, combinations thereof, or the like can provide differing malleable characteristics of the mounting wing 210.

Advantageously, the channels 212 can allow the mounting wing 210 to be shaped to match the differing curvatures of the patients' skin surface. Notably, the mounting wing 210 can be shaped, and remain in that shape once applied to the skin surface. By contrast, mounting wings without the channels 212 elastically return to their original shape, i.e. substantially flat, thereby distorting the skin surface to which they are adhered to. Moreover, the channels 212 allow the same device to be used in a range of situations, positions on the body, or types of patient. For example a wrist portion of a child defines a more acute radius of curvature than that of an adult leg. Alternatively, the skin of the elderly is more delicate and deforms more readily. Accordingly, channels 212 allow the device 100 to fit comfortably to different areas of the patient and accommodate these variations.

Nose Griping and Deflection

Figure 2E:
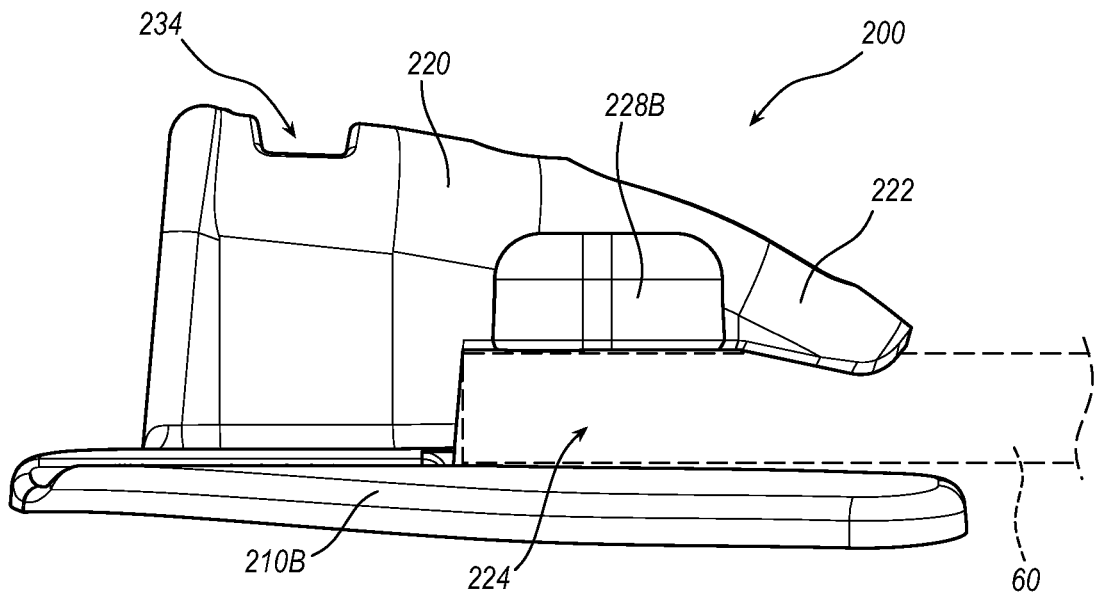
FIG. 2E shows a side view of a retainer, in accordance with embodiments disclosed herein.
Figure 2F:
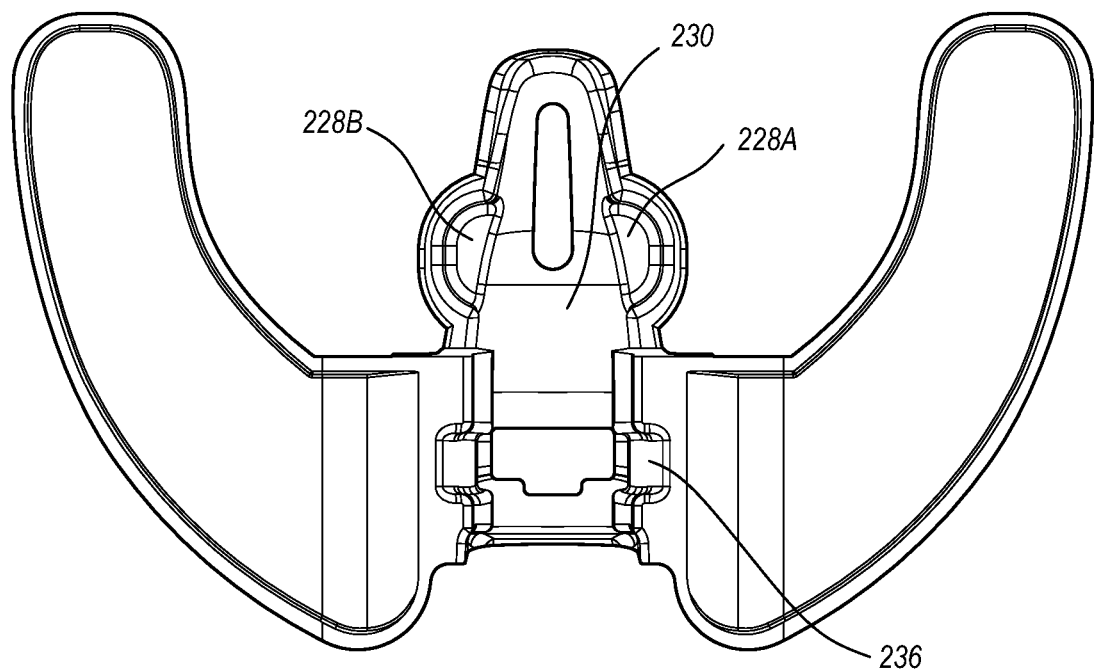
FIG. 2F shows an underside plan view of a retainer, in accordance with embodiments disclosed herein.

In an embodiment, as shown in FIGS. 1E, 2E-2F, the retainer body 220 further includes a nose portion ("nose") 222.

As shown in FIGS. 2A and 2E, in an embodiment, the nose portion 222 defines a "cutaway" recess 224, extending transversely between the nose 222 and a skin surface and extending laterally between the left mounting wing 210A and the right mounting wing 210B. The recess 224 is configured to receive an anti-microbial disc 60. Worded differently, the retainer 200 including the recess 224 can be configured to retain and stabilize a portion of the catheter 300 without disturbing an anti-microbial disc 60 disposed at the insertion site 80. In an embodiment, the nose portion 222 can be angled downward and configured to impinge against the antimicrobial disc 60 to retain the disc 60 in an interference fit between the nose 222 and the skin surface. Advantageously, the retainer 200 can secure the disc 60 in place and allow a clinician to change out disc 60 as needed without disturbing the securement device 100, catheter 300 or the like.

In an embodiment, the angled nose portion 222 can be configured to constrain the catheter strain relief 330 and deflect it in a slightly downward direction. As shown in FIG. 1E, the angle (θ) of the downward bend imposed by the nose 222 is predetermined and can vary according to various factors. The angle of the nose 222 also allows the catheter hub 310 to be positioned substantially parallel to the skin surface 50. Advantageously, with the catheter hub 310 positioned substantially flat against the skin surface of the patient, this further stabilizes that catheter hub 310 relative to the skin surface and prevents rocking, pistoning, or cantilevering, of the catheter, as described herein. Further, with the catheter hub 310, and associated extension sets, etc. aligned parallel with a skin surface, this provides a lower profile and prevents the hub 310 from protruding from the skin surface and catching on items of clothing, bandages, or the like. Further details of exemplary retainers and associated structures can be found in U.S. Pat. Nos. 7,014,627 and 8,740,852, and U.S. Publication No. 2017/0326340, each of which is incorporated by reference in its entirety into this application.

Catheter Hub Rotation Prevention

Figure 2G:
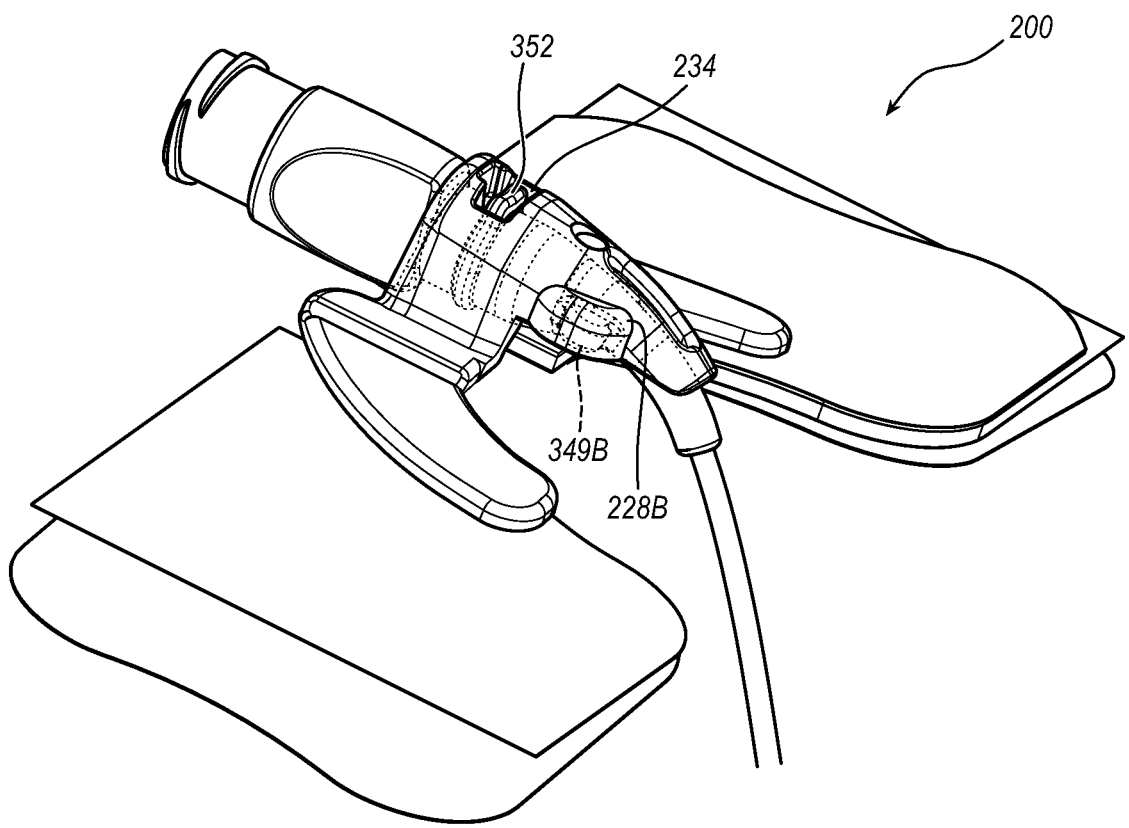
FIG. 2G shows a perspective view of a catheter securement device including a catheter disposed therein, in accordance with embodiments disclosed herein.
Figure 2H:
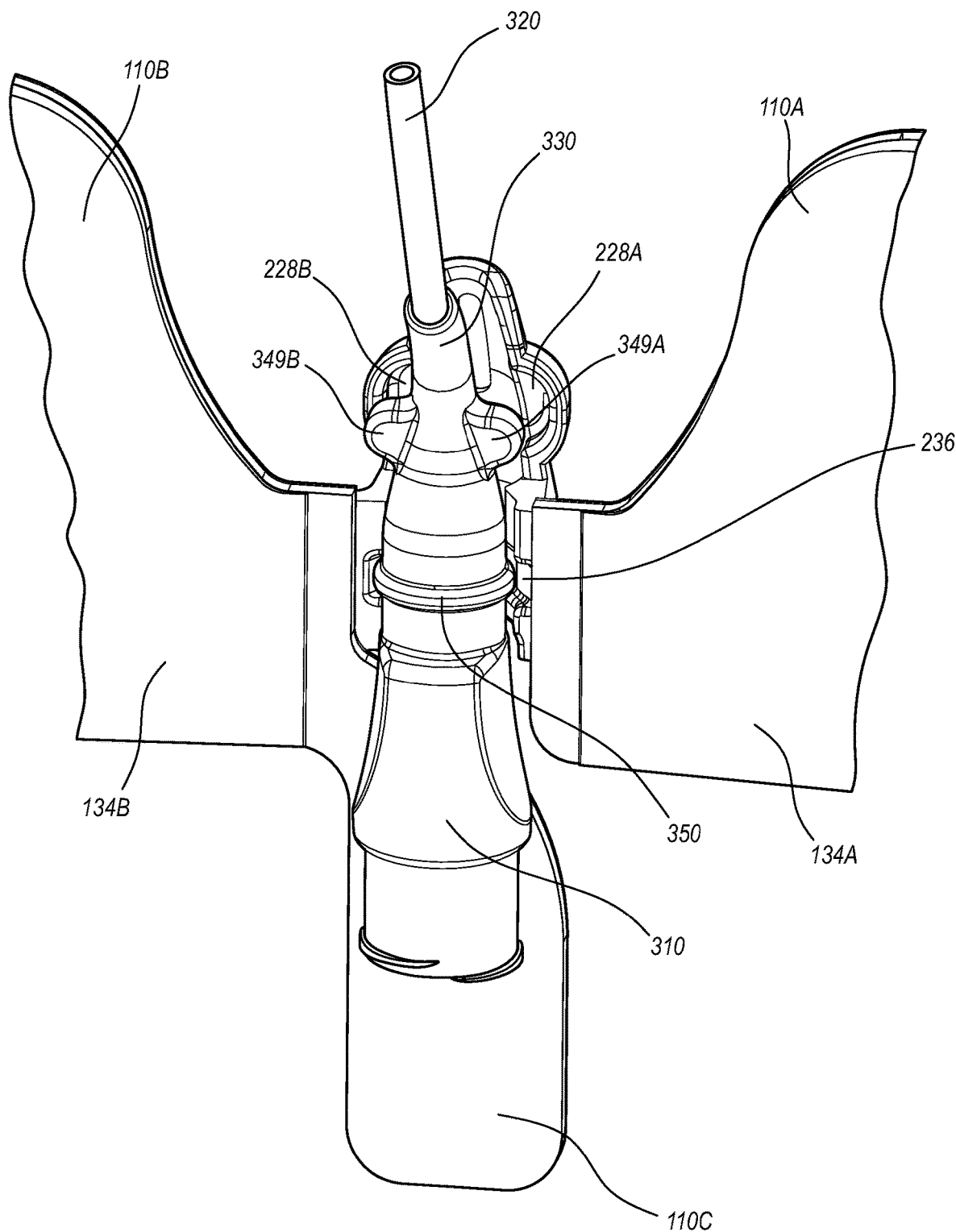
FIG. 2H shows an underside exploded view of a retainer including anchor pads and a catheter, in accordance with embodiments disclosed herein.

As shown in FIGS. 2F-2H, the retainer 200 can include one or more anti-rotation features that inhibits rotation or "roll" of the catheter 300 about the longitudinal axis. In an embodiment, the retainer 200 can include a pocket 228, for example a left pocket 228A and a right pocket 228B, which can be configured to receive a nub 349, for example a left nub 228A and a right nub 228B, disposed on the catheter 300. The nub 349 can be a protrusion that extends perpendicularly to the longitudinal axis and engages the pocket 228 to inhibit rotational movement of the catheter 300, relative to the retainer 200, about the longitudinal axis. In an embodiment, the nubs 349 can engage the pockets 228 in a snap-fit, interference-fit, press-fit, or similar engagement to secure the catheter 300 within the retainer 200. In an embodiment, the retainer 200 further includes an alignment channel 236 configured to receive an alignment ring 350 disposed on the catheter 300. In an embodiment the alignment ring 350 can be disposed annularly about the catheter hub 330. The alignment channel 236 can be configured the receive the alignment ring 350 to ensure the catheter 300 is correctly seated within the retainer 200, and to inhibit longitudinal movement of the catheter 300 relative to the retainer 200.

In an embodiment, the retainer 200 further includes a lock window 234 configured to receive a lock tab 352 extending from the catheter 300. In an embodiment, the lock tab 352 extends from the catheter hub 310, perpendicular to a longitudinal axis of the catheter 300. The locking tab 352 can engage the locking window 234 to inhibit movement of the catheter 300 relative to the retainer 200, for example rotational movement, lateral movement, longitudinal movement, combinations thereof, and the like. Advantageously, the one or more anti-rotation features such as the nubs 349, pockets 228, locking tab 352, locking window 234, alignment ring 350 and alignment channel 236 can inhibit movement of the catheter 300, to further reduce rocking, pistoning, and/or kinking of the catheter tube 320. Further, the one or more anti-rotation features can allow a clinician to determine that the catheter 300 is correctly seated within the retainer 200 without visual confirmation, i.e. by tactile confirmation. Advantageously, this can expedite correct placement of the catheter 300 within the securement device 100.

In an embodiment, the lock tab 352 can include a different color from that of the retainer 200, catheter assembly 300, or the like so as to provide easy visual confirmation to a clinician when the catheter 300 is correctly seated within the retainer 200. As shown in FIG. 2G, in an embodiment, the retainer 200 can be formed of a transparent, translucent, or semi-translucent material to allow a clinician to view the position of the catheter 300, disposed therebelow, relative to the retainer 200. This can facilitate positioning the catheter 300 relative to the retainer 200. In an embodiment, the retainer 200 can include a viewing window 238, or aperture, communicating between the channel 230 and an outer surface of the retainer 200 to allow a clinician to observe the catheter 300 disposed therebelow. In an embodiment, a colored portion of the catheter 300 can align with the viewing window 238 to indicate that the catheter 300 is correctly seated within the retainer 200. Advantageously, this can expedite correct placement of the catheter 300 within the securement device 100.

Advantageously, one or more anti-rotation features described herein allow a user to attach or detach medical lines, syringes, extension sets, and the like to/from the catheter hub 310 with only one hand. Often the connectors that couple to the catheter hub 310 require some sort of twisting motion to fully engage or disengage therefrom. Typically a clinician would require one hand to stabilize the catheter while attaching/detaching the catheter hub with the other. Embodiments disclosed herein stabilize the catheter 300 and allow a user to attach/detach items to/from the catheter hub single handedly.

Anchor Pad

Figure 3C:
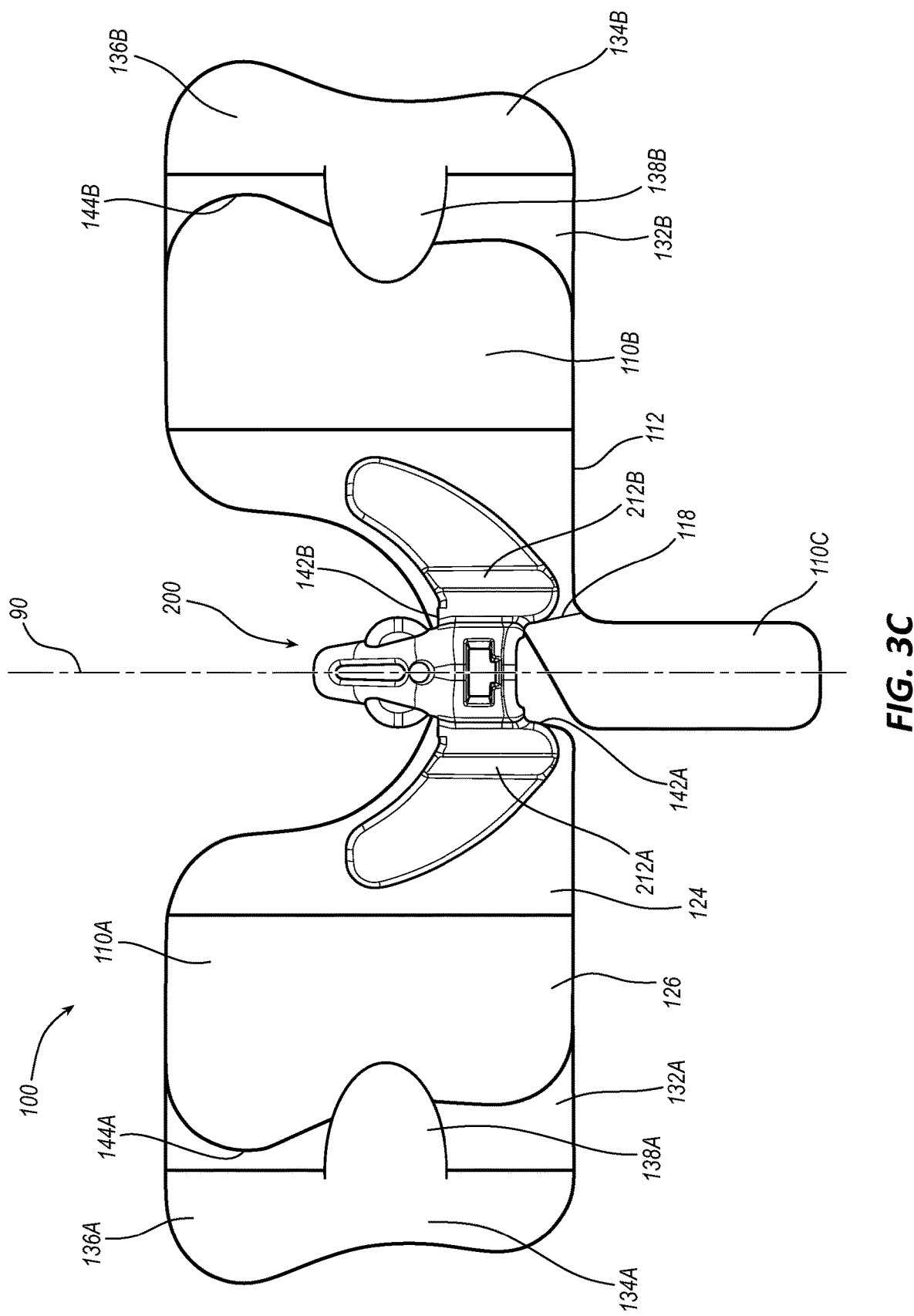
FIG. 3C shows a plan view of the catheter securement device of FIG. 3A, in accordance with embodiments disclosed herein.

FIGS. 3A-3E show various details of the anchor pad 110 and associated structures. As shown in FIGS. 3A-3B, the anchor pad(s) 110 can be formed of one or more layers of material. For example, the anchor pad 110 can be formed of a foam portion 124 and can include an overlying fabric portion 126 such as polyester fiber, medical gauze, or the like. An adhesive layer 128 can be applied on a bottom, skin-facing, surface of the anchor pad 110 to allow the securement device 100 to adhere to a skin surface 50 of a patient. In an embodiment, the foam layer 124 can extend over a portion of the anchor pad 100. In an embodiment, the fabric portion 126 can extend over a portion of the anchor pad 110. In an embodiment, the adhesive layer 128 can extend over a portion of the anchor pad. A release liner 130 can be disposed on the adhesive layer 128 to protect the adhesive layer 128 during handling and transport.

In an embodiment, as shown in FIG. 3A, 3C, an outer perimeter 122 of the anchor pad 110 can be defined by the fabric portion 126, with the foam portion 124, extending over only a portion of the anchor pad 110. The adhesive layer 128 can extend over a lower surface of the fabric layer 126, foam layer 124, or combinations thereof. Optionally, the outer perimeter 122 of the anchor pad 110 can be defined by the foam portion 124 with the fabric portion 126, extending over a portion of the anchor pad 110.

In an embodiment, the mounting wing 210 can be disposed on an upper surface of the anchor pad 110 and secured thereto. In an embodiment, the mounting wing 210 can be disposed between one or more layers that form the anchor pad 110 and secured therebetween. For example, a portion of the mounting wing 210 can be disposed between the fabric layer 126 and the foam layer 124, or between the foam layer and the adhesive layer 128. As such, the mounting wing 210 can be attached to the anchor pad 110 on both an upper surface and a lower surface of the mounting wing 210. This further secures the mounting wing 210 to the anchor pad 110. These and other combinations of anchor pad construction are contemplated to fall within the scope of the present invention.

In an embodiment, the anchor pad 110 includes a scalloped portion 116, for example a left scalloped portion 116A and a right scalloped portion 116B. The scalloped portion 116 can be configured to match a radius of curvature of the antimicrobial disc 60, and/or a portion of the mounting wing 210. The disc 60 can then be received between the scalloped portions 116A, 116B of the anchor pads 110A, 110B respectively to contact the skin surrounding the insertion site 80.

Protective Pad

Figure 3D:
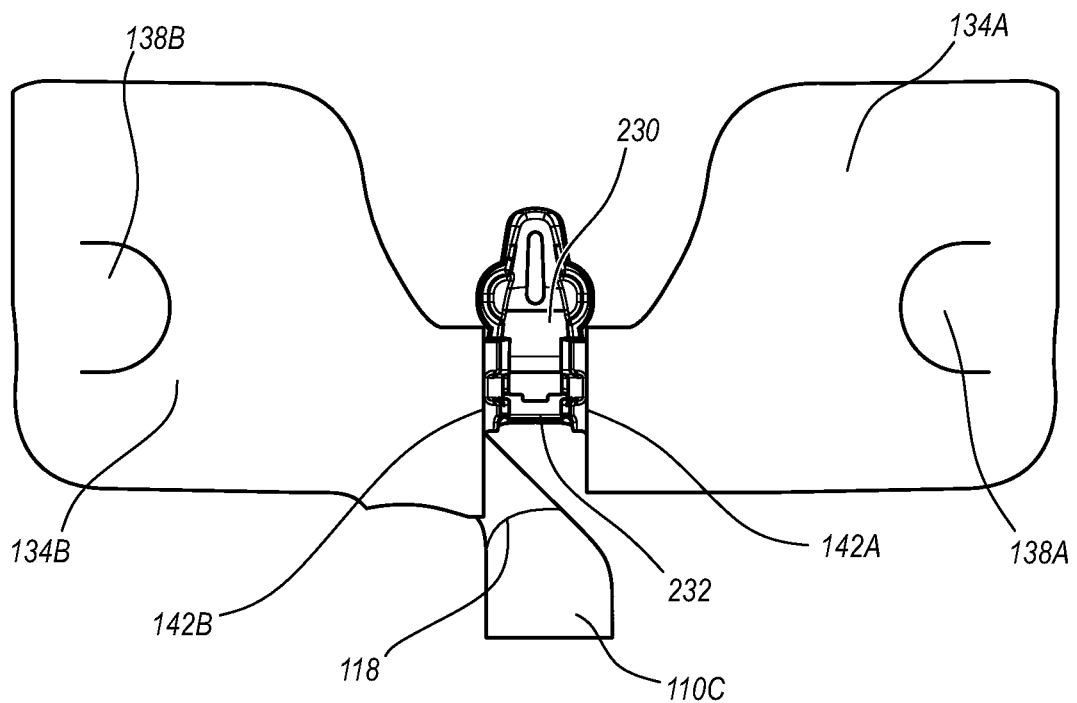
FIG. 3D shows an underside plan view the catheter securement device of FIG. 3A, in accordance with embodiments disclosed herein.

As shown in FIGS. 3A, 3C-3D, in an embodiment, the securement device 100 further includes a protective pad 110C. The protective pad 110C can be integrally formed with either of a left anchor pad 110A or a right anchor pad 110B, or both. In an embodiment, the protective pad 110C can be a separate structure from that of anchor pads 110A, 110B. The protective pad 110C can be formed of similar materials to the anchor pad 110, as discussed herein. For example, the protective pad 110C can be formed of a foam material. In an embodiment, the protective pad 110C can include an adhesive layer disposed on at least a portion of a lower surface thereof. In an embodiment, the thickness of the protective pad 110C can be the same as the anchor pads 110A, 110B. In an embodiment, the thickness of the protective pad 110C can be different from the anchor pads 110A, 110B. In an embodiment, the protective pad 110C is thicker than anchor pads 110A, 110B so as to provide increased cushioning between the patients skin and the catheter 300, extension set 70, retainer 200, or combinations thereof.

In an embodiment, as shown in FIGS. 3C-3D, the protective pad 110C is removably attached to either of the left or right anchor pad 110A, 110B. As shown in FIGS. 3C-3D, the protective pad 110C can include a tear line 118 to facilitate detachment of the protective pad 110C from the anchor pad 110. In an embodiment the protective pad 110C and anchor pad 110 can be integrally formed and a tear line 118, such as a perforation, score line, laser cut line, or the like, can be formed therein. In an embodiment, the protective pad 110C and anchor pad 110 can be formed as separate structures and attached thereto along tear line 118 using adhesive, bonding, welding, or similar suitable techniques that facilitate detachment along the tear line 118.

In an embodiment, a laterally central axis of the protective pad 110C substantially aligns with the laterally central axis 90 of the device 100. The protective pad 110C extends proximally from a proximal edge 112 of the anchor pads 110A, 110B. In an embodiment, the protective pad 110C extends to a point that is proximal of the spin nut 72. The protective pad 110C can also extend laterally from a central axis to a lateral edge of the catheter 300. In an embodiment, the protective pad 110C extends to an outer-most lateral edge of the spin nut 72. In an embodiment the protective pad 110C extends beyond an outer-most lateral edge of the catheter 300, extension set 70, spin nut 72 or combinations thereof, so that a width of the protective pad 110C is greater than a width of the medical article. The protective pad 110C can be positioned so that it is substantially below the connection of the extension set 70 with the catheter 300.

Advantageously, the protective pad 110C protects the patients' skin from abrasions, pressure ulcers, or the like, caused by the retainer 200, extension set 70, spin nut 72, or luer lock, etc. For example, the spin nut 72 often includes protrusions or ribs to facilitate grip, however these protrusions can cause pressure ulcers when pressed or rubbed directly against the patients' skin. It will be appreciated that other portions of the extension set 70, catheter hub 310, retainer 200, or connecting portions therebetween can also include protrusions, edges, or the like that can cause similar problems for the patient. Accordingly, the protective pad 110C protects the patients' skin from such trauma. Further, the protective pad 110C can be easily detached should the pad be unnecessary or obstruct the medical article.

The protective pad 110C can further include release agent disposed on at least a portion of an upper surface thereof. In an embodiment, the release agent can be formed as a layer disposed on an upper surface or can be integrated with the material forming the protective pad 110C. The release agent can prevent an adhesive from sticking to an upper surface of the protective pad 110C. For example, portions the securement device 100 can be covered by a polyurethane dressing to provide a barrier and prevent infection. Such dressings often include an adhesive lower surface for adhering to the device, catheter, associated structures, and a skin surface of the patient. When such a dressing is removed, the release agent prevents the dressing from adhering to the upper surface of the protective pad 110C. This in turn prevents portion of the medical article, disposed between the dressing and protective pad, from being disturbed as the dressing is removed, thereby avoiding patient discomfort, dislodgment of the catheter, disruption of fluid flow, or the like.

Release Liner

Referring to FIGS. 3A-3E, in an embodiment, the anchor pad 110 includes a release liner 130 disposed on a lower surface thereof. For example, a left release liner 130A and a right release liner 130B are disposed on a lower surface of the left anchor pad 110A and right anchor pad 110B, respectively. In an embodiment, each of the release liners 130A, 130B includes a first portion 132 and a second portion 134. The first portion 132 extends laterally from an outer edge 144 of the anchor pad 110 towards a central axis 90 of the device 100, to a lateral inner edge 142 of the anchor pad. In an embodiment, the first portion 132 defines an outer perimeter shape which can be similar to an outer perimeter shape of the anchor pad 110 so as to cover an entire lower surface of the anchor pad 110 and any adhesive layer disposed thereon. In an embodiment, the outer perimeter of the first portion 132 extends beyond the outer perimeter of the anchor pad 110 along at least one edge. As such, the release liner 130 also protects an edge surface of the anchor pad, and any adhesive layers disposed thereon. For example, as shown in FIG. 3C, a first portion 132B of the right release liner 130B defines an outer perimeter shape that is similar to the outer perimeter shape of the right anchor pad 110B, further a right side perimeter of the first portion 132B also extends laterally beyond an outer perimeter 116 of the anchor pad 110 so as to protect a side surface thereof.

In an embodiment, the first and second portions 132, 134 of the release liner 130 are attached along a join line disposed along a lateral inner edge 142 of the anchor pad 110. In an embodiment the join line extends along an edge of the release liner that is proximate the central axis 90, although other edges of the release liner 130 are also contemplated and fall within the scope of the present invention. In an embodiment, first and second portions 132, 134 are formed separately and attached along the join line using adhesive, bonding, welding, mechanical fasteners, or similar suitable attachments. In an embodiment, first and second portions 132, 134 are formed as a single monolithic piece 130 and a join line 142 is formed therein by folding, scoring, perforation, laser cutting, or similar suitable methods.

In an embodiment, the second portion 134 extends from the join line, disposed along the lateral inner edge 142 to a lateral outer edge 144 of the anchor pad 110. In an embodiment, the second portion 134 extends laterally beyond the lateral outer edge 144 of the anchor pad 110. For example, as shown in FIG. 3C, the second portion 134B of the right release liner 130B extends laterally from the join line, disposed at the lateral inner edge 142B, to a point disposed laterally beyond a lateral outer edge 144B of the anchor pad 110B. In an embodiment, the second portion 134 can define a similar outer perimeter shape to the first portion 132 such that when the two portions are attached and folded against each other, along the join line, the first and second portions 132, 134 define a substantially similar outer perimeter shape. In an embodiment, the first and second portions 132, 134 can define different outer perimeter shapes. In an embodiment, the second portion 134 can extend from the lateral inner edge 142, beyond the lateral outer edge 144, to provide a pull tab 136, e.g. right pull tab 136B. In an embodiment, pull tab 136 can be formed integrally with the second portion 134, as a single monolithic piece and formed of the same material. In an embodiment, the pull tab 136 can be a separate structure from that second portion 134 and coupled thereto using adhesive, bonding, welding, or similar suitable attachment means. As such, the pull tab 136 can be formed of a different material from that of the release liner 130, and can provide differing properties, such as a different color, texture, or mechanical properties.

Clasping Feature

As shown in FIGS. 1A-1B, 3C-3E, in an embodiment, the release liner 130 includes a clasping feature 138 located adjacent a lateral outer edge 144 of the anchor pad 110. The clasping feature 138 can be configured to maintain the second portion 134, pull tab 136, or combinations thereof in a predetermined position that is accessible to the user and prevents the second portion 134 from obstructing the opening 232 of the channel 230. In an embodiment, the clasping feature 138 can releasably attach the second portion 134 to the lateral outer edge 144 of the anchor pad 110, to a lateral outer edge of the first portion 132, or combinations thereof. In an embodiment, the clasping feature 138 can be a flap attached to the second portion 134, and can extend toward the central axis 90. In an embodiment, the clasping feature 138 can be formed as a separate structure from the second portion 134 and attached thereto using adhesive, bonding, welding, or similar suitable attachment means.

As shown in FIG. 3D, the clasping feature 138 can be a U-shaped cut formed in a portion of the release liner 130. It will be appreciated that other shapes and sizes of flap are also contemplated and fall within the scope of the present invention. In an embodiment the flap of the clasping feature 138 is formed integrally with the second portion 138 by forming a substantially U-shaped die cut flap in the second portion 134 of the release liner.

Figure 3E:
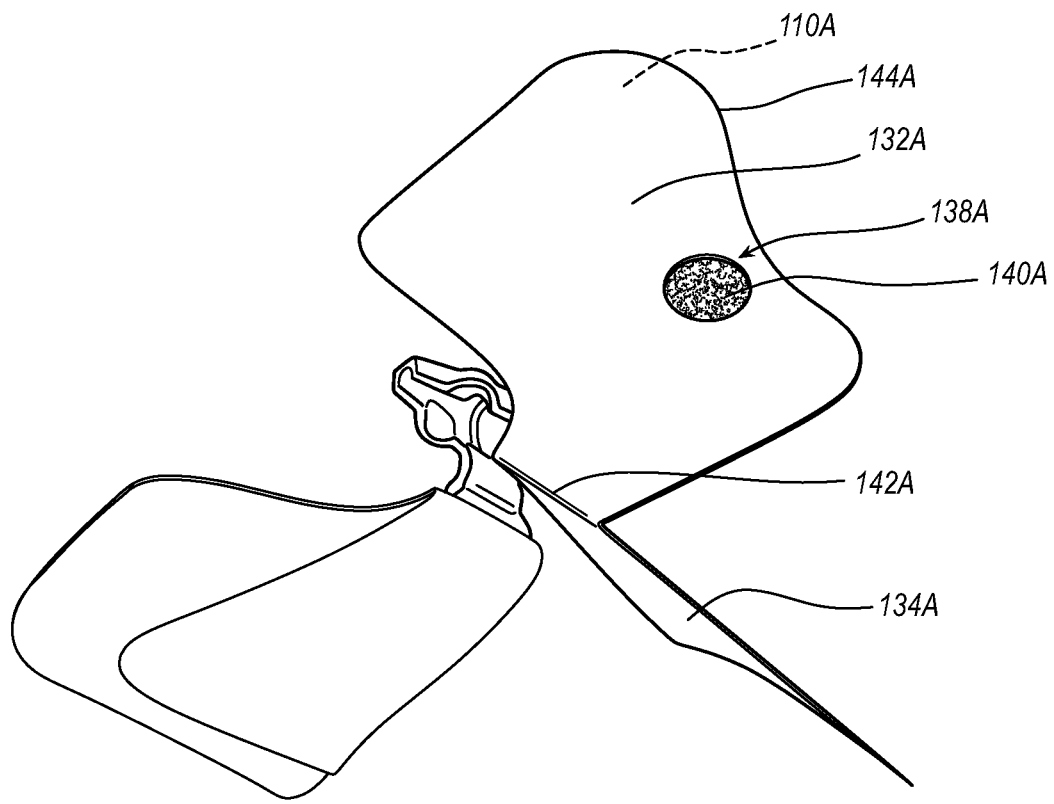
FIG. 3E shows an underside view the catheter securement device of FIG. 3A, in accordance with embodiments disclosed herein.

As shown in FIG. 3E, in an embodiment, the clasping feature 138 is formed as an aperture 140 in the release liner first portion 132. For example, the clasping feature 138A includes an aperture 140A disposed in the left release liner first portion 132A. The aperture exposes a portion of the adhesive layer 128, disposed on an underside of the anchor pad 110A. The release liner second portion 134B can fold back over the aperture 140A, as described herein. A surface of the second portion 134A can then adhere to the portion of adhesive layer 128 of the anchor pad 110A, releasably attaching the second portion 134A thereto. In an embodiment, the clasping feature 138 can include an adhesive spot disposed between the first and second portions 132, 134 of the release liner.

Embodiments of the clasping feature 138, as described herein can hold the second portion 134 adjacent the first portion 132 and anchor pad 110. This keeps the second portion 134 from protruding downwards from the device, snagging on objects and obstructing a lower, longitudinal opening 232. For example, as shown in FIGS. 1A-1B, 2H, embodiments of the clasping feature 138 hold the second portion 134 substantially flat against first portion 132, providing a clear entryway for the ingress/egress of a medical article to the retainer 200 of the device.

Method of Use

In an exemplary method of use, a catheter securement device 100 is provided including a retainer 200, an anchor pad 110 and a release liner 130, as described herein. A distal portion of a catheter 300 can be inserted into a vasculature of a patient. An external portion of the catheter 300 can then be retained and stabilized by the securement device 100. As the device 100 is lowered on to the catheter external portion, the release liner second portion 134 is maintained in a substantially horizontal orientation and prevented from obstructing the opening 232 by the clasping feature 138. The clasping feature 138 also maintains the position of the pull tab 138 as extending laterally beyond the release liner first portion and anchor pad 110.

With the securement device 100 situated correctly on a skin surface of the patient, the clinician is able to grasp the pull tab 136 and urge the release liner second portion 134 laterally outward. This causes the clasping feature 138 to detach from the release liner first portion 132/anchor pad 110. The second portion 134, which is also attached to the first portion 132 at a join line at a lateral inner edge 142, peels the first portion away from the anchor pad 110 from the lateral inner edge 142 towards the lateral outer edge 144, exposing an adhesive layer to the skin surface of the patient. Each of the left and right anchor pads can be adhered to the skin of the patient in a sequential manner.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A securement device for stabilizing an elongate medical article on a skin surface of a patient, comprising:
   a retainer comprising:
   a retainer body defining a channel aligned with a central axis of the securement device, and configured to receive a portion of the elongate medical article; and
   a mounting wing supporting the retainer body;
   an anchor pad supporting the mounting wing, including
   an adhesive layer disposed on a lower surface of the anchor pad, and defining an outer edge and an inner edge disposed laterally opposite the outer edge; and a release liner including a first portion disposed on the adhesive layer and extending from the outer edge to the inner edge, and a second portion coupled to the first portion along the inner edge and extending from the inner edge to the outer edge, the release liner including a clasping feature configured to releasably secure the second portion to the first portion proximate the outer edge.

2. The securement device according to claim 1, wherein the first portion of the release liner is disposed between the second portion and the adhesive layer, and the second portion of the release liner extends laterally outward from the outer edge to define a pull tab.

3. The securement device according to claim 1, wherein the clasping feature includes a flap die cut into the second portion of the release liner and configured to releasably secure the second portion to one of the first portion of the release liner or the anchor pad.

4. The securement device according to claim 1, wherein the clasping feature includes an aperture disposed in the first portion of the release liner, and configured to allow an upper surface of the second portion of the release liner to contact the adhesive layer, releasably securing the second portion thereto.

5. The securement device according to claim 1, wherein the anchor pad includes a fabric upper layer, and a central foam layer extending over at least part of the anchor pad and disposed between the fabric upper layer and the adhesive layer.

6. The securement device according to claim 1, further including a protective pad extending from a proximal edge of the anchor pad, aligned with the central axis of the securement device and disposed between the elongate medical device and the skin surface of the patient.

7. The securement device according to claim 6, wherein the protective pad includes a central foam layer and a release agent disposed on an upper surface thereof, and wherein the protective pad is configured to mitigate abrasions to the skin surface caused by the elongate medical device.

8. The securement device according to claim 6, wherein the protective pad further includes a tear line disposed between the protective pad and the anchor pad and configured to selectively release the protective pad from the anchor pad.

9. The securement device according to claim 1, wherein the elongate medical device is a midline catheter, a dialysis catheter, a Central Venous Catheter ("CVC"), a Peripherally Inserted Central Catheter ("PICC"), a Peripherally Inserted Venous catheters ("PIV"), a Foley catheter, a urinary catheter, a feeding tube, or a balloon catheter.

10. A securement device for stabilizing an external portion of a catheter assembly after insertion of an internal portion of the catheter assembly into a body of a patient via a catheter insertion site, the securement device comprising:
a retainer body defining a channel;
a first mounting wing and a second mounting wing supporting the retainer body, a distal edge of the first mounting wing and the second mounting wing extending distally beyond the catheter insertion site;
a first anchor pad and a second anchor pad, the first anchor pad supporting the first mounting wing, the second anchor pad supporting the second mounting wing, one of the first anchor pad or the second anchor pad including an adhesive layer disposed on a lower surface thereof;
a release liner including a first portion disposed on the adhesive layer and a second portion coupled to the first portion, the release liner including a clasping feature configured to releasably secure the second portion to the first portion; and
a protective pad disposed proximally of the first anchor pad and the second anchor pad and disposed between the external portion of the catheter assembly and a skin surface of the patient.

11. The securement device according to claim 10, wherein the first mounting wing and the first anchor pad adheres to a first portion of the skin surface adjacent the catheter insertion site, and the second mounting wing and the second anchor pad adheres to a second portion of the skin surface adjacent the catheter insertion site, opposite the first portion of the skin surface, the first mounting wing and the second mounting wing stabilizing the catheter insertion site, disposed therebetween, relative to the catheter assembly.

12. The securement device according to claim 10, wherein one of the first mounting wing or the second mounting wing includes a channel configured to impart malleable characteristics thereon.

13. The securement device according to claim 12, wherein a thickness of the first mounting wing or the second mounting wing within the channel is between 0.010 in. and 0.020 in.

14. The securement device according to claim 10, wherein the retainer body, the first mounting wing and the second mounting wing are configured to mitigate rocking or pi stoning of the catheter assembly.

15. The securement device according to claim 10, wherein a nose portion of the retainer body includes a cutaway portion configured to retain an anti-microbial disc between the nose portion and the catheter insertion site.

16. The securement device according to claim 15, wherein the nose portion is configured to deflect a strain relief of the catheter assembly at a predetermined angle and an axis of the external portion of the catheter assembly extends substantially parallel to the skin surface of the patient.

17. The securement device according to claim 15, wherein the first mounting wing and the second mounting wing are configured to receive the anti-microbial disc therebetween.

18. The securement device according to claim 10, further including an anti-rotation feature configured to inhibit rotation of the catheter assembly relative to the retainer body and to align the catheter assembly with the retainer.

19. The securement device according to claim 18, wherein the anti-rotation feature includes one of a pocket, alignment channel, or a locking window configured to engage one of a nub, alignment ring, or locking tab disposed on the catheter assembly.

20. The securement device according to claim 10, wherein the retainer body is formed of one of a transparent, translucent, or semi-translucent material, and is configured to allow a clinician to view a position of the catheter assembly therebelow.

21. The securement device according to claim 10, wherein the retainer body includes a viewing window communicating between the channel and an outer surface thereof and configured to allow a user to observe the external portion of the catheter assembly disposed therebelow.

22. The securement device according to claim 21, wherein the catheter assembly includes a colored portion configured to align with the viewing window to indicate that the external portion of the catheter assembly is correctly aligned with the retainer body.

23. The securement device according to claim 10, wherein the protective pad is configured to inhibit trauma to the skin surface from the external portion of the catheter assembly.

24. A method of securing a catheter assembly, comprising:
providing a securement device, comprising:
a retainer body defining a channel configured to receive at least a portion of the catheter assembly;
a mounting wing supporting the retainer body;
an anchor pad coupled to the mounting wing and including an adhesive layer disposed on a lower surface thereof; and
a release liner including a first portion disposed on the adhesive layer, and a second portion integrally formed with the first portion along a first edge and extending laterally outward to a second edge, opposite the first edge, the release liner further including a clasping feature;
receiving the portion of the catheter assembly within the channel;
positioning a bottom surface of the securement device against a skin surface of a patient;
urging the second portion of the release liner laterally outward;
peeling the first portion of the release liner away from the adhesive layer from the first edge to the second edge; and
adhering the retainer body to the skin surface of the patient.

25. The method according to claim 24, further including releasably securing the second portion of the release liner to the first portion of the release liner proximate the second edge with the clasping feature.

26. The method according to claim 25, wherein the clasping feature is a flap that is die cut into the second portion of the release liner.

27. The method according to claim 25, wherein the clasping feature is an aperture disposed in the first portion of the release liner that allows a portion of the adhesive layer to contact the second portion of the release liner.

28. The method according to claim 24, wherein the second portion of the release liner extends laterally outward beyond the second edge to define a pull tab.

29. The method according to claim 24, further including positioning a protective pad between a second portion of the catheter assembly and the skin surface of the patient, the protective pad extending proximally from a proximal edge of the anchor pad and releasably coupled thereto.

30. The method according to claim 24, further including sliding an anti-microbial disc longitudinally proximally between a nose portion of the retainer body and the skin surface, the nose portion angled to impinge on the anti-microbial disc and retain the anti-microbial disc therebetween.

31. The method according to claim 24, further including bending the mounting wing from a first position to a second position, the mounting wing including a channel configured to impart malleable characteristics so that the mounting wing remains in the second position until repositioned.

* * * * *